United States Patent [19]
Lakowicz et al.

[11] Patent Number: 5,660,991
[45] Date of Patent: Aug. 26, 1997

[54] LONG LIFETIME ANISOTROPY (POLARIZATION) PROBES FOR CLINICAL CHEMISTRY, IMMUNOASSAYS, AFFINITY ASSAYS AND BIOMEDICAL RESEARCH

[76] Inventors: Joseph R. Lakowicz, 10037 Fox Den Rd., Ellicott City, Md. 21042; Henryk Szmacinski, 8401 Glen Rd., Baltimore, Md. 21234; Ewald Terpetschnig, 4308 Forest View Ave., Baltimore, Md. 21206

[21] Appl. No.: 330,743

[22] Filed: Oct. 28, 1994

[51] Int. Cl.$^6$ .................. G01N 33/53; G01N 33/533; G01N 33/536
[52] U.S. Cl. .................. 435/7.1; 435/7.93; 436/546; 436/164; 436/172
[58] Field of Search .................. 435/7.1, 7.93, 435/968, 7.5, 501, 536, 546, 164, 172

[56] References Cited

U.S. PATENT DOCUMENTS

| | | | |
|---|---|---|---|
| 4,816,419 | 3/1989 | Halfman | 436/546 |
| 5,239,057 | 8/1993 | Wang et al. | 530/321 |

FOREIGN PATENT DOCUMENTS

| | | |
|---|---|---|
| 222341 | 5/1987 | European Pat. Off. . |
| 312897 | 4/1989 | European Pat. Off. . |
| WO 90/05301 | 5/1990 | WIPO . |

*Primary Examiner*—Ponnathapura Achutamurthy
*Attorney, Agent, or Firm*—Rothwell, Figg, Ernst & Kurz, P.C.

[57] ABSTRACT

A method of conducting an immunoassay of a sample of interest is described, including the steps of (A) coupling a luminescent asymmetric metal-ligand complex to the sample of interest to form a coupled sample, (B) exciting the coupled sample with linearly polarized electromagnetic energy to cause the coupled sample to emit fluorescent light; and (C) measuring the polarization of the fluorescent emission as a measure of a biological characteristic of the sample of interest.

30 Claims, 21 Drawing Sheets

LONG LIFETIME ANISOTROPY (POLARIZATION) PROBES FOR CLINICAL CHEMISTRY, IMMUNOASSAYS, AFFINITY ASSAYS AND BIOMEDICAL RESEARCH

FIELD OF THE INVENTION

The present invention relates to the field of fluorescent anisotropy (polarization) probes for immunoassays and the like and, more particularly, to a method of conducting an immunoassay using a fluorescent metal-ligand complex which can be coupled to proteins and which also displays a long lifetime and a high initial anisotropy or polarized fluorescence.

BACKGROUND OF THE INVENTION

Presently, fluorescence polarization (anisotropy) immunoassays, which are based on the polarization or anisotropy of emitted light when a sample is excited with vertically polarized light, are widely used in clinical chemistry but are limited to the analysis of low molecular weight antigens such as drugs. This limitation exists because the short lifetime of the fluorescent probes preclude their use with larger, high molecular weight antigens which rotate more slowly in solution than do the smaller antigens.

With respect to metal-ligand complexes, there have been many reports which attempt to determine whether the excited state is distributed among the organic ligands on a rather symmetric complex, or whether it is localized between the metal and one of the ligands. This is an important distinction, because the former model predicts a low anisotropy, while the latter model predicts a higher anisotropy. An expert in the field would predict a low anisotropy, as symmetric molecules typically display low anisotropies, and metal ions in solution typically display zero anisotropies. Given the possibility of different effects which could account for loss of anisotropy, it was not clear that complexes such as Ru-metal-ligand complexes (Ru-MLC) would display useful anisotropy values. Also, even if the anisotropies were non-zero, it was not clear whether complexes such as Ru-MLC would display anisotropies which depend on molecular size, as needed for a fluorescence polarization immunoassay (FPI), or whether they would become depolarized by transfer of the excited state energy among the ligands, and thus would be independent of molecular size or rotational diffusion. Therefore, in regard to metal-ligand complexes, there has been no recognition of their use as fluorescent probes for biomedical applications.

The following references represent the state of the art of fluorescent polarization immunoassay:

*Measurement of Angiotensinogen in Human Serum By Fluorescence Polarization Immunoassay*, David B. Gordon, Clin. & Exper. Hyper.—Theory and Practice, A10(3), 1988, pages 485–503.

*Immunoassay—Innovations in Label Technology*, Joan H. Howanitz, M. D., Arch. Pathol. Lab. Med., Volume 112, August 1988, pages 775–779.

*Four Fluorescent Polarization Immunoassays for Therapeutic Drug Monitoring Evaluated*, Virginia M. Havre et al, Clinical Chemistry, Volume 35, No. 1, 1989, pages 138–140.

*New Fluorescent Derivatives of Cyclosporin for Use in Immunoassays*, M. T. French et al, Journal of Pharmaceutical & Biomedical Analysis, Volume 10, No. 1, 1992, pages 23–30.

*A Decade of Development of Immunoassay Methodology*, James P. Gosling, Clinical Chemistry, Volume 36, No. 8, 1990, pages 1408–1427.

*Fluoroimmunoassay: Present Status and Key Problems*, Erkki Soini et al, Clinical Chemistry, Volume 25, No. 3, 1979, pages 353–361.

*Fluorescent Excitation Transfer Immunoassay*, Edwin F. Ullman et al, The Journal of Biological Chemistry, Volume 251, No. 14, Jul. 25, 1976, pages 4172–4178.

*Fluorescence Polarization in Immunochemistry*, W. B. Dandliker et al, Immunochemistry, Volume 7, 1970, pages 799–828.

*Photophysics of Ruthenium Complexes Bound to Double Helical DNA*, Challa V. Kumar et al, Journal American Chemical Society, Volume 107, No. 19, 1985, pages 5518–5523.

The following references represent the state of the art of time-resolved immunoassay:

*Time-Resolved Fluorometry in Immunoassay*, T. Lovgren et al, Alternative Immunoassays, 1985, pages 203–217.

*Current Concepts and Future Developments*, R. P. Ekins, Alternative Immunoassays, 1985, pages 219–237.

*Immunoassays with Time-Resolved Fluorescence Spectroscopy: principles and Applications*, Eleftherios P. Diamandis, Clinical Biochemistry, Volume 21, June 1988, pages 139–150.

*Europium Chelate Labels in Time-Resolved Fluorescence Immunoassays and DNA Hybridization Assays*, Eleftherios P. Diamandis et al, Analytical Chemistry, Volume 62, No. 22, Nov. 15, 1990, pages 1149–1157.

*Europium as a Label in Time-Resolved Immunofluorometric Assays*, Ilkka Hemmila et al, Analytical Biochemistry, 137 (1984), pages 335–343.

*Phosphorescent Immunoassay, Are Metalloporphyrins an Alternative to Rare Earth Fluorescent Labels?*, A. P. Savitskii et al, Doklady Akademii Nauk SSSR, 1989, pages 48–51.

*Fiber-Optic Time-Resolved Fluorimetry for Immunoassays*, Randy D. Petrea et al, Talanta, Volume 35, No. 2, 1988, pages 139–144.

*Applications of Lanthanide Chelates for Time-Resolved Fluoroimmunoassay*, Philip Mottram et al, American Chemical Laboratory, May/June 1990, pages 34–38.

U.S. Pat. No. 4,374,120 Feb. 15, 1983 Soini et al
U.S. Pat. No. 4,745,076 May 17, 1988 Muller et al The following references disclose the known spectral properties of transition metal-ligand complexes:

*Design and Applications of Highly Luminescent Transition Metal Complexes*, J. N. Demas et al, Analytical Chemistry, Volume 63, No. 17, Sep. 1, 1991, pages 829–837.

*Novel Fluorescent Label for Time-Resolved Fluorescence Immunoassay*, Richard B. Thompson et al, SPIE, Volume 909, Time-Resolved Laser Spectroscopy in Biochemistry, 1988, pages 426–433.

*Redox Properties of Ruthenium(II) Tris Chelate Complexes Containing the Ligands 2,2'-Bipyrazine, 2,2'-Bipyridine, and 2,2'-Bipyrimidine*, D. Paul Rillema et al, Inorganic Chemistry, Volume 22, No. 11, 1983, pages 1617–1622.

*Localization of Electronic Excitation Energy In $Ru(2,2'$-$Bipyridine)_2(2,2'$-$Bipyridine$-$4,4'$-$Dicarboxylic\ Acid)^{2+}$ and Related Complexes*, James Ferguson et al, Chemical Physics Letters, Volume 68, No. 1, pages 21–24.

*Energy Transfer from Luminescent Transition Metal Complexes to Oxygen*, J. N. Demas et al, Journal of the American Chemical Society, May 25, 1977, pages 3547–3551.

The following references are of further background interest with respect to the present invention:

U.S. Pat. No. 4,565,790 Jan. 21, 1986 Hemmila et al
U.S. Pat. No. 4,837,169 Jun. 6, 1989 Toner
U.S. Pat. No. 4,962,045 Oct. 9, 1990 Picozza et al
U.S. Pat. No. 5,089,423 Feb. 18, 1992 Diamandis et al
U.S. Pat. No. 5,202,270 Apr. 13, 1993 Ungemach et al
U.S. Pat. No. 5,221,605 Jun. 22, 1993 Bard et al
U.S. Pat. No. 5,221,611 Jun. 22, 1993 Stenglein et al
U.S. Pat. No. 5,061,857 Oct. 29, 1991 Thompson et al
U.S. Pat. No. 5,083,852 Jan. 28, 1992 Thompson
U.S. Pat. No. 5,094,819 Mar. 10, 1992 Yager et al

*Thin Layers of Depolarizers and Sensitizers*, Lasovsky et al, Chem. Abstract 106, 1987: 95354n.

*Time-Resolved Photoselection of $[Ru(bpy)_3]^{2+}$-exciton Hopping in the Excited State*, Myrick et al, J. Amer. Chem. Soc. 109, 1987: 2841–2842.

*Circularly polarized Luminescence of Tris-Bipyridine Ruthenium (II) Complexes at Low Temperature*, Tsubomura et al, Chem. Abstract 112, 1990: 65776h.

The present inventors wish to stress that none of the experts listed above have suggested complexes such as Ru or Os metal-ligand complexes for use in fluorescence polarization immunoassays. We refer to the emission from these complexes as fluorescence, primarily for convenience. The exact nature of the excited state is unknown, and the emission may be regarded as fluorescence or phosphorescence.

As indicated above, FPIs are presently limited to low molecular weight analytes, such as drugs and hormones, as admitted in Urios et al, "Adaptation of Fluorescence Polarization Immunoassay to the Assay of Macromolecules", *Analytical Biochemistry*, 185, 308–312 (1990) (which used $F_{ab}$ fragments having a molecular weight near 40,000, as opposed to a full IgG (Immunoglobin G, human) molecule having a molecular weight near 160,000) and Tsuruoka et al, "Fluorescence Polarization Immunoassay Employing Immobilized Antibody", *Biosensors & Bioelectronics*, 6, 501–505 (1991) (which bound the Ab to colloidal gold to increase its molecular weight in an attempt to change the correlation time of the larger antigens). With respect to Tsuruoka in particular, the present inventors do not consider its approach to be useful, since the molecular weight of the antibody is already too high for the lifetime of the label. In this regard, it is noted that the lifetimes of the probes are near 4 ns.

The limitation to low molecular weight analytes arises because the FPIs depend on a change in the apparent molecular weight of a fluorescently-labeled antigen upon binding to the antibody. A change in "apparent molecular weight" results upon binding to the large antibody molecule because the smaller antigen is now bound to the larger antibody molecule. Typical molecular weights of antigen and antibody are 1,000 and 160,000 daltons, respectively. The limitation to low molecular weight antigens is due to the short lifetimes of probes used in present FPIs and can be circumvented by using longer lifetime fluorophores. However, few such long-lived probes are known. The review articles mention pyrene derivatives, which display lifetimes near 100 ns. However, pyrene requires UV excitation near 320 nm, is photosensitive, and displays a low polarization. UV excitation results in significant autoflourescence from biological samples. A further advantage of the RuMLCs is their high chemical and photochemical stability.

To assist in understanding the above-described limitation and the present invention, some examples are set forth below. The need for a change in apparent molecular weight can be seen from the following example calculation. Suppose the labeled antigen has a molecular weight of 1,000 daltons, which results in a rotational correlation time of about 0.5 ns. The molecular weight of the antibody IgG is 160,000, resulting in a rotational correlation time near 100 ns (v+h≈1.5, see eq. 8 below). The anisotropy of a fluorophore or labeled macromolecule is given by $$r = \frac{r_0}{1 + \tau/\Theta} \quad (1)$$

where $r_0$ is a constant typically near 0.3, $\tau$ is the lifetime and $\Theta$ is the rotational correlation time.

For present immunoassays, the lifetimes of the probes are near 4 ns. The anisotropy of the free and antibody-bound antigens are thus as follows:

$$\text{Free } Ag: r = \frac{0.3}{1 + 4/0.5} = 0.033$$

$$\text{Bound } Ag: r = \frac{0.3}{1 + 4/100} = 0.288 \, (\% \text{ change} = 773\%)$$

Hence, a large change in anisotropy is found upon binding of Ag to Ab for low molecular weight antigens.

The favorable change described above is not obtained for high molecular weight antigens. Suppose the molecular weight of the antigen is about 160,000, with a correlation time of 100 ns, and the molecular weight of the antibody is about 450,000, with a correlation time of 300 ns. The correlation time of the antigen-antibody complex will be near 400 ns. For the presently-used short lifetime fluorophores, the anisotropy values will be as follows:

$$\text{Free } Ag: r = \frac{0.3}{1 + 4/100} = 0.288$$

$$\text{Bound } Ag: r = \frac{0.3}{1 + 4/400} = 0.297 \, (\% \text{ change} = 3\%)$$

This change in anisotropy is small because the lifetime is much shorter than the correlation time of the antigen.

The present invention provides a long lifetime label with good $r_0$ values. In particular, data show lifetimes near 400 ns. For the larger molecular weight Ag-Ab complex (($\Theta$=400 ns), the expected anisotropy values are as follows:

$$\text{Free } Ag: r = \frac{0.3}{1 + \frac{400}{100}} = 0.060$$

$$\text{Bound } Ag: r = \frac{0.3}{1 + \frac{400}{400}} = 0.15 \, (\% \text{ change} = 150\%)$$

The change in anisotropy for the 400 ns lifetime is 150%, which is much improved as compared to only 3% for the 4 ns lifetime. Also, many antigens of interest (e.g., IgM) are still larger (MW=950,000, $\Theta \geq 600$ ns), which will yield still higher anisotropy (r=0.180, % change=200%). It should be noted that the % change in anisotropy is more important than the absolute values.

In order to avoid confusion, it should be noted that polarization (P) and anisotropy (r) describe the same phenomena, and are related as follows:

$$P = \frac{I_\parallel - I_\perp}{I_\parallel + I_\perp} \quad (2)$$

-continued $$r = \frac{I_\| - I_\perp}{I_\| + 2I_\perp} \quad (3)$$

where $I_\|$ and $I_\perp$ are the vertically and horizontally polarized components of the emission, when excited with vertically polarized light. The polarization and anisotropy are related by $$r = \frac{2P}{3-P} \quad (4)$$

$$P = \frac{3r}{2+r} \quad (5)$$

The parameters P and r are both in common use. The values of P are used more often in FPI because they are entrenched by tradition and are slightly larger than the anisotropy values. The parameter r is preferred on the base of theory. Both P and r are related to the correlation time and/or molecular volume as follows:

$$\frac{r_0}{r} = 1 + \frac{\tau}{\Theta} = 1 + \frac{kT}{\eta V} \tau \quad (6)$$

$$\left(\frac{1}{P} - \frac{1}{3}\right) = \left(\frac{1}{P_0} - \frac{1}{3}\right)\left(1 + \frac{kT}{\eta V} \tau\right) \quad (7)$$

$$= \left(\frac{1}{P_0} - \frac{1}{3}\right)(1 + \tau/\Theta)$$

In these equations k is the Boltzmann constant, T is the temperature (K), $\eta$ is the viscosity and V is the molecular volume. The correlation time is related to the molecular weight (M) of the protein as follows:

$$\Theta = \frac{\eta M}{RT} (\bar{v} + h) \quad (8)$$

where R is the ideal gas constant, $\bar{v}$ is the specific volume of the protein and h is the hydration, typically 0.2 g $H_2O$ per gram of protein.

SUMMARY OF THE INVENTION

We have synthesized a new type of protein labeling reagent or probe which has desirable features for use in immunoassays, clinical chemistry and biomedical research, i.e., a fluorescent metal-ligand complex which can be coupled to proteins and which also displays a long lifetime and high anisotropy or polarization in the absence of rotational diffusion. The value is often referred to as the initial or fundamental anisotropy ($r_o$) or polarization ($P_o$). This reagent or probe also has the advantage of having fluorescent emission in the red region of the spectrum, and can be excited with simple light sources or visible-wavelength lasers, both of which are desirable from the standpoint of reducing auto-fluorescence and instrument cost and complexity. The spectral characteristics and long lifetime of such probes also allow fluorescence lifetime measurements with simple exciting-light sources, such as a flash lamp, laser diode, blue LED or a blue electroluminescent lamp. The long luminescence lifetime allows the probe to be used for immuno-chemical polarization or intensity assays of high molecular weight species. The use of complexes such as Ru or Os metal-ligand complexes allows fluorescence polarization immunoassays to be performed on high molecular weight antigens (MW>1000), which is not routinely possible with other fluorophores.

Thus, our invention provides a long luminescence lifetime which, in turn, allows the assay of higher molecular weight antigens by the polarization or anisotropy method. The use of luminescent metal-ligand complexes for fluorescence polarization assays has, to our knowledge, not been earlier proposed, because such complexes typically display low anisotropies (polarizations). Also, it was not known whether the luminescence from these complexes was depolarized due to rotational motion, which is required for a fluorescence polarization immunoassay, or due to internal randomization of the excited state energy within the complex. The latter behavior makes a probe unsuitable for use in a fluorescence polarization immunoassay. In contrast, the asymmetric complex used in our invention displays a high polarization because of the presence of non-identical ligands.

Another advantage of our invention is that a fluorescence polarization immunoassay can be accomplished in a manner comparable to so-called "time-resolved immunoassays". Thus, background auto-fluorescence is suppressed by gating the fluorescence detector on at long times, after decay of the initial auto-flourescence, which typically decays in 5 ns. With the shorter lived probes of the prior art, such gating is not technologically practical, and it is not advantageous because the probe decays on the same timescale as the auto-flourescence. Gating is very advantageous and practical when using the long lifetime luminescence metal complexes of our invention.

Thus, our invention creates a new class of fluorescence polarization immunoassays for use with high molecular weight antigens, while allowing suppression of auto-fluorescence by time-gating of the fluorescence detector. These novel probes find use in biochemical and biomedical research for measuring the rotational dynamics of high molecular weight species, particularly membrane-bound proteins. Advantages include the use of an inexpensive light source and simple instrumentation because of the long lifetime, thereby allowing bedside clinical chemistry and the assay of high molecular weight antigens.

Accordingly, the present invention provides a method of conducting an immunoassay of a sample of interest, comprising the steps of:
  coupling a luminescent asymmetric metal-ligand complex to the sample of interest to form a coupled sample;
  exciting the coupled sample with linearly polarized electromagnetic energy to cause the coupled sample to emit partially polarized fluorescent light; and
  measuring the polarization of the fluorescent light emission as a measure of a biological characteristic of the sample of interest.

In addition, the present invention provides a fluorescence polarization assay for quantifying the amount of an analyte in a sample, comprising the steps of:
  (a) mixing (1) an asymmetric metal-ligand complex conjugated to a molecule which specifically binds the analyte with (2) the sample;
  (b) exciting the mixture of step (a) with linearly polarized light to cause the complex to emit polarized light;
  (c) measuring the polarization of the light emitted by the complex;
  (d) calculating the amount of analyte in the sample by correlating the polarization measured in step (c) with the polarization of light emitted from a control sample containing a known amount of analyte.

Also, the present invention provides a competitive fluorescence polarization immunoassay for quantifying the amount of an analyte in a sample, comprising the steps of:
  (a) mixing (1) a control containing a known amount of analyte conjugated to an asymmetric metal-ligand complex with (2) a molecule which specifically binds the analyte;

(b) exciting the mixture of step (a) with linearly polarized light to cause the complex to emit polarized light;

(c) measuring the polarization of the light emitted by the complex;

(d) adding the sample to the mixture to form a new mixture including analyte not conjugated which competes with the analyte conjugated to the asymmetric metal-ligand complex in binding to the molecule which specifically binds the analyte, thereby causing a change in polarization;

(e) measuring the change in polarization;

(f) calculating the amount of analyte in the sample by correlating the change in polarization with the control containing a known amount of analyte.

Additionally, the present invention provides a method of conducting an affinity polarization assay of a sample of interest to quantify the amount of an analyte in the sample, comprising the steps of:

(a) mixing (1) a control containing a known amount of analyte conjugated to an asymmetric metal-ligand complex with (2) a molecule which has affinity for the analyte;

(b) exciting the mixture of step (a) with linearly polarized light to cause the complex to emit polarized light;

(c) measuring the polarization of the light emitted by the complex;

(d) adding the sample to the mixture to form a new mixture including analyte not conjugated which competes with the analyte conjugated to the asymmetric metal-ligand complex in associating with the molecule which has affinity for the analyte, thereby causing a change in polarization;

(e) measuring the change in polarization;

(f) calculating the amount of analyte in the sample by correlating the change in polarization with the control containing a known amount of analyte.

DETAILED DESCRIPTION OF THE INVENTION

There are a number of metal-ligand complexes which display luminescence, including complexes containing Co, Cr, Cu, Mo, Ru, Rh, W, Re, Os, Ir, and Pt. In particular, transition metal complexes, especially those with Ru, Os, Re, Rh, Ir, W and Pt, can be used. The metal in the metal-ligand complex is particularly preferably selected from the group consisting of ruthenium, osmium, and rhenium. A suitable ligand in the metal-ligand complex can be polypyridine, bipyridine, or a related compound, and the ligand can contain a reactive group commonly used for linkage to biological molecules, such as a N-hydroxysuccinimide ester of a carboxylic acid, haloacetyl groups, maleimides, sulfonyl chlorides, and isothiocyanates.

Other ligands for such metal-ligand complexes are bipyrazyl, phenanthroline, and related substituted derivatives, or inorganic ligands such as CO, Cl, nitrile and isonitrile.

Suitable metal-ligand complexes (MLCs) for use in fluorescence polarization immunoassays and affinity assays according to the present invention are set forth below.

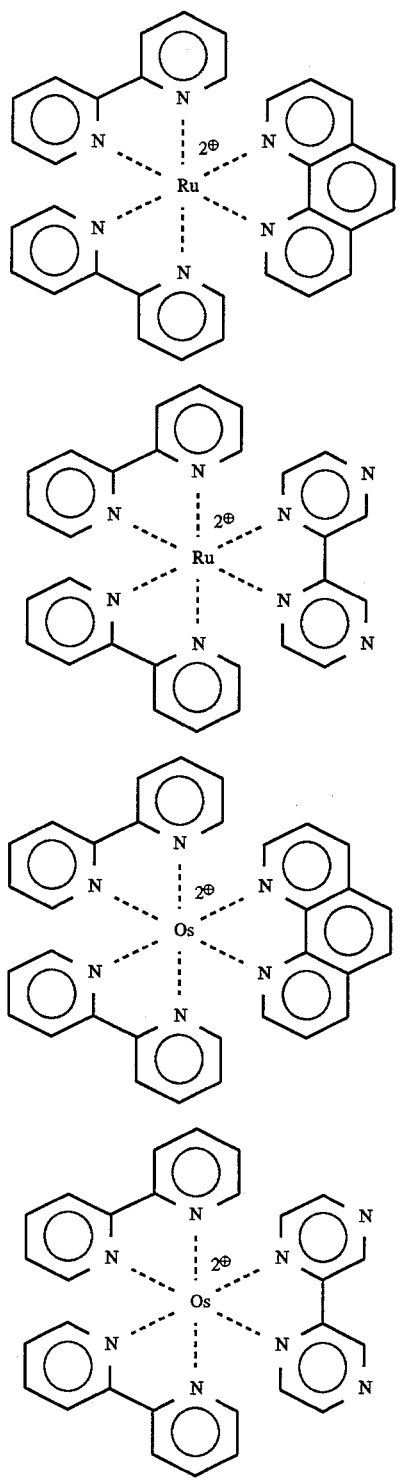

MLC-1

MLC-2

MLC-3

MLC-4

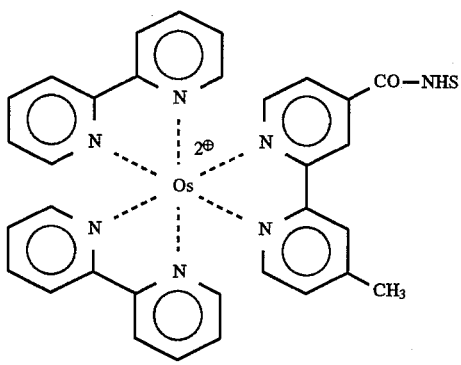

MLC-5

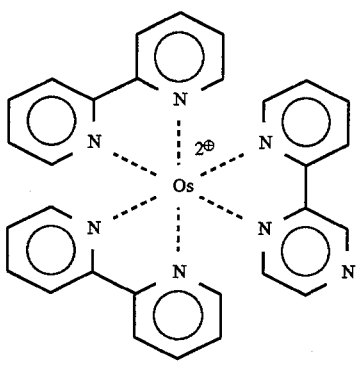

MLC-6

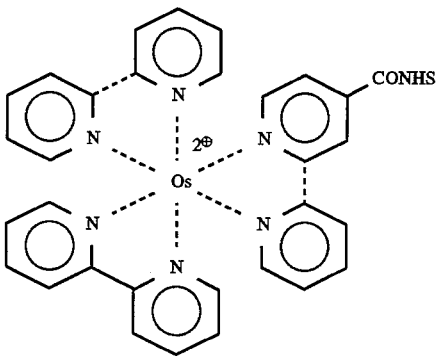

MLC-7

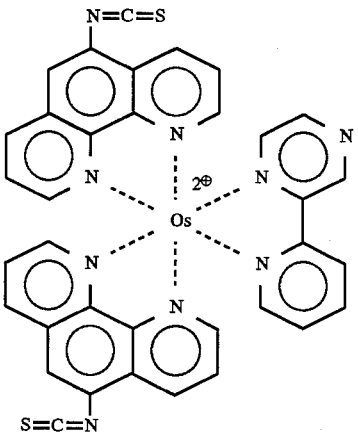

MLC-8

MLC-9 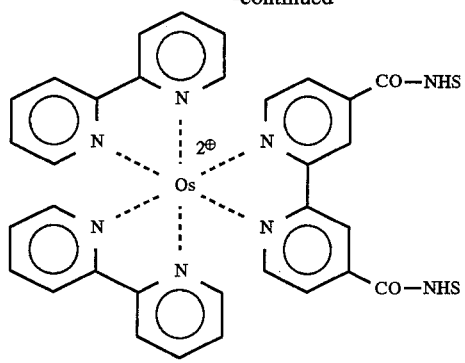
MLC-13 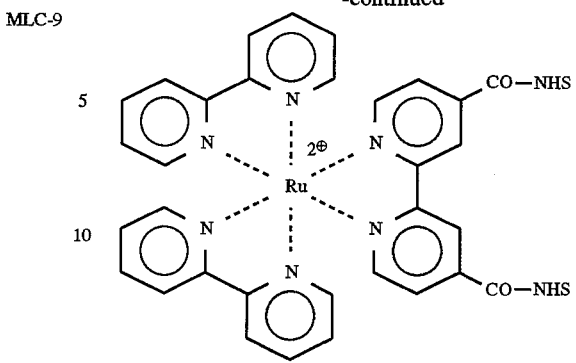
MLC-10 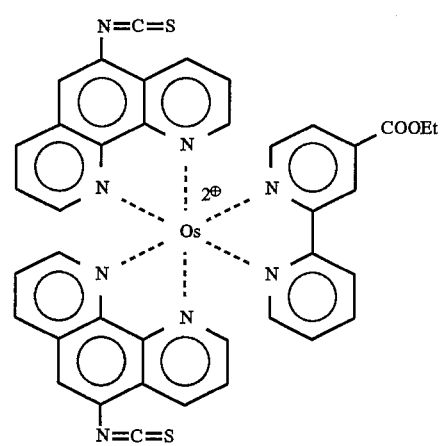
MLC-14 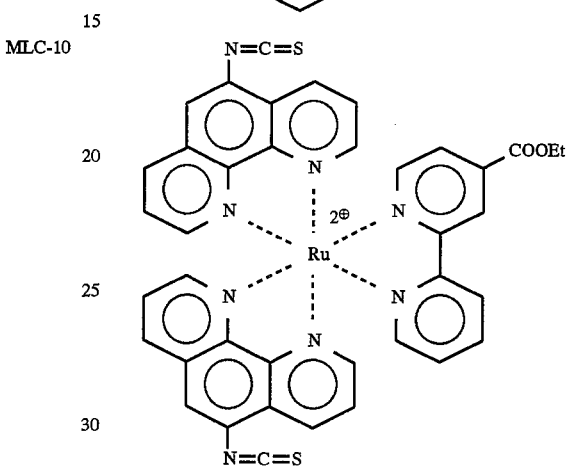
MLC-11 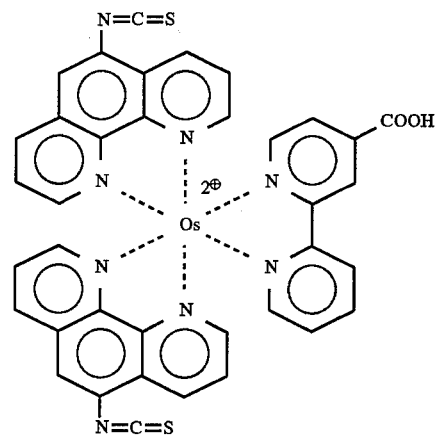
MLC-15 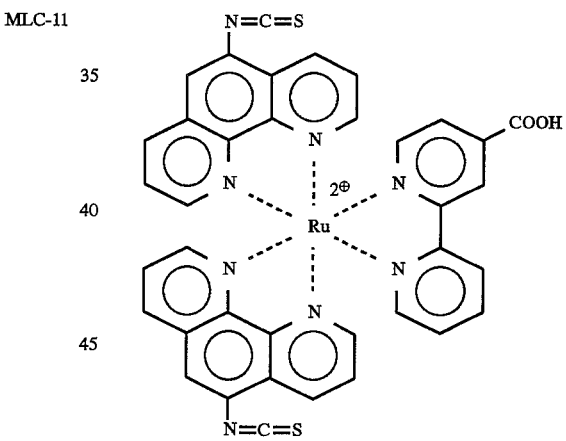
MLC-12 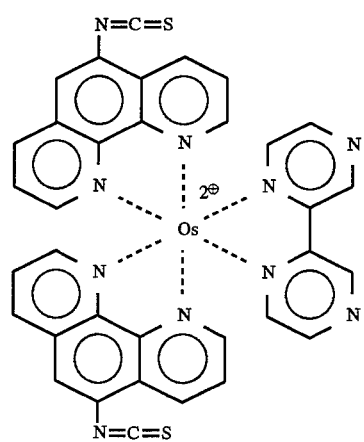
MLC-16 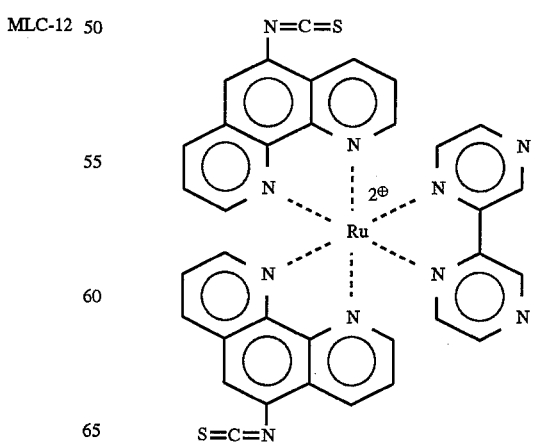

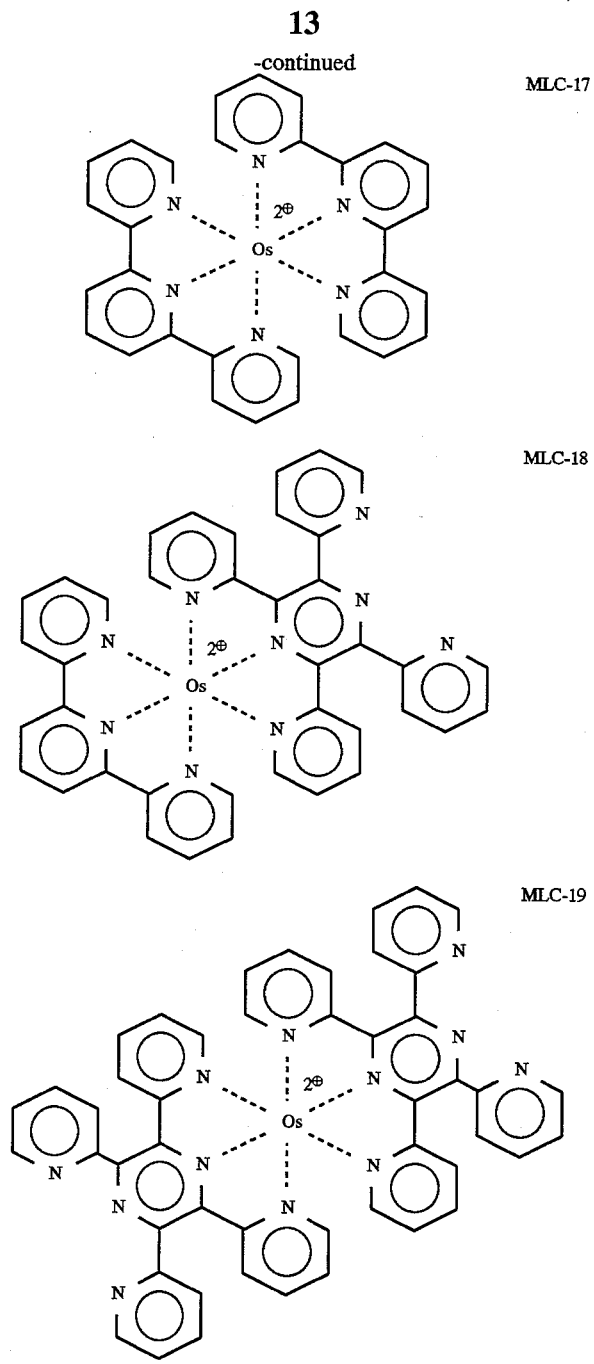

Figure 3:
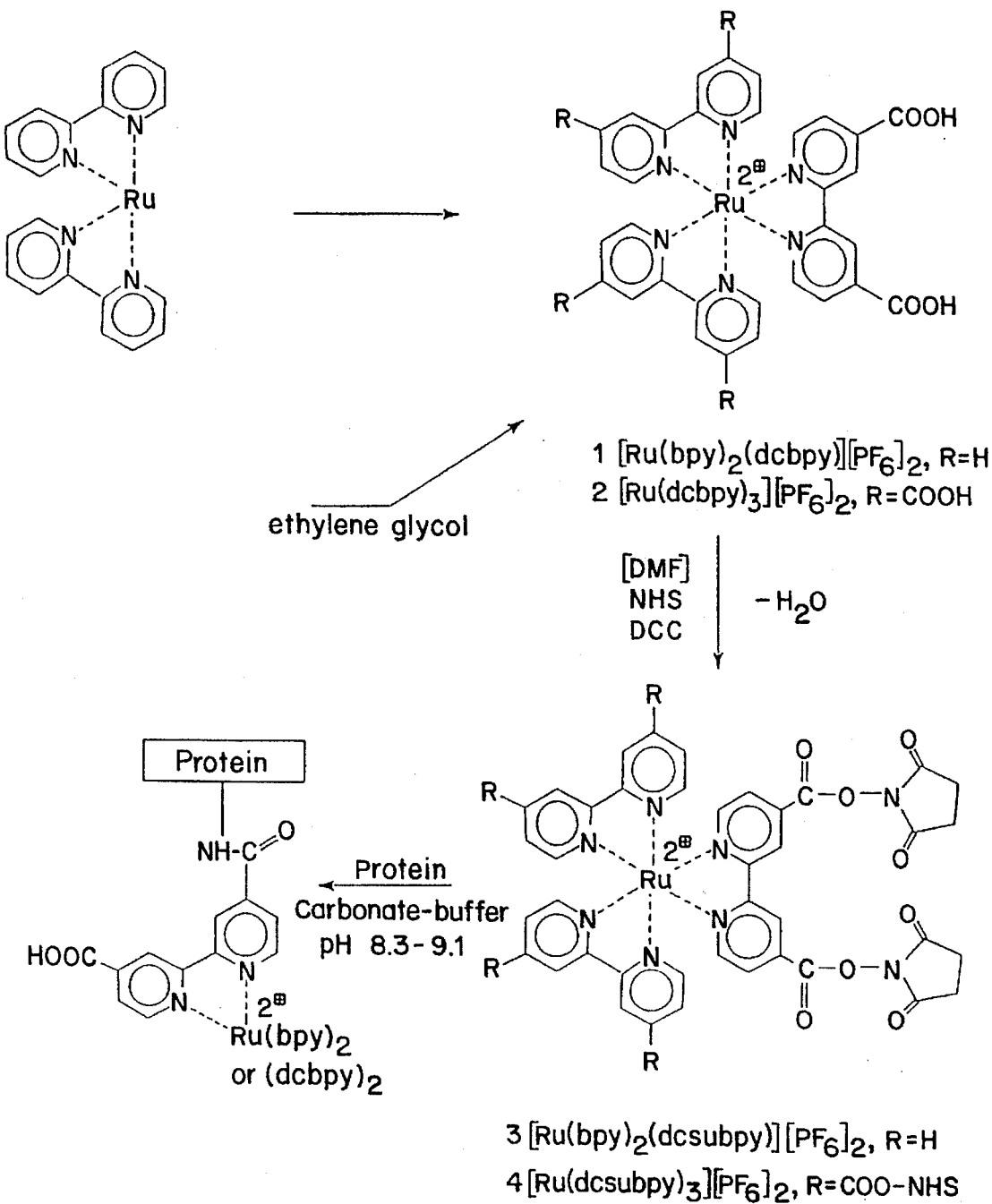
FIG. 3 describes the synthesis of a Ru metal-ligand complex which is suitable for covalent attachment to proteins.

The complexes used in the present invention can be synthesized according to the scheme set forth in FIG. 3. A discussion of this figure and the other figures is set forth below.

Figure 1:
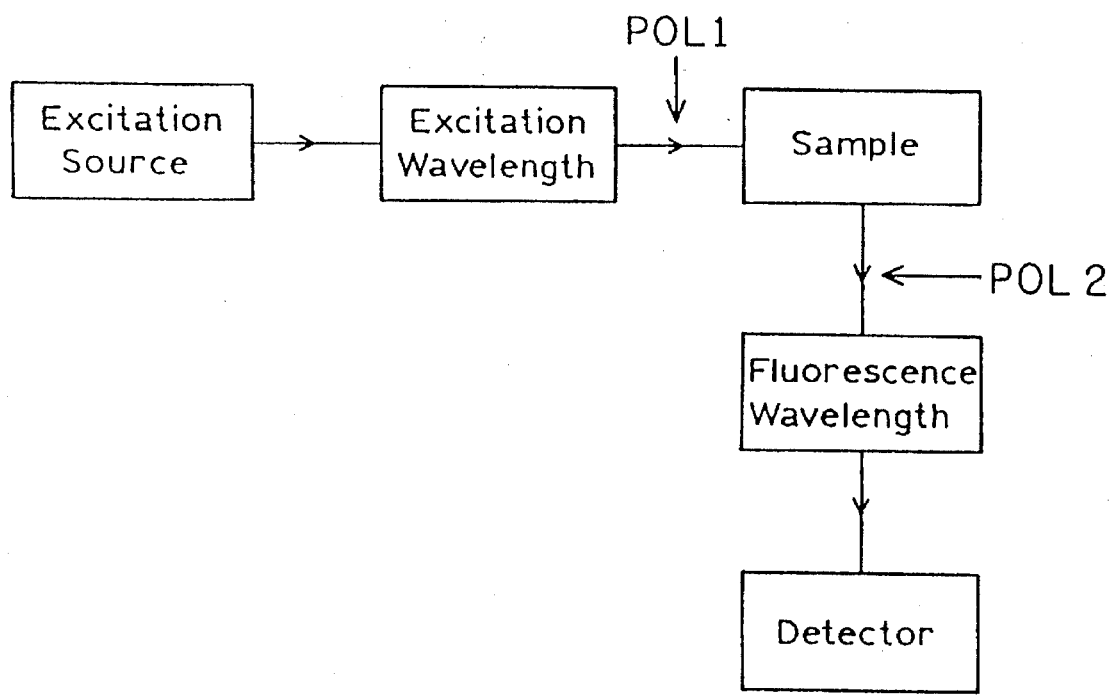
FIG. 1 is a schematic block diagram of an apparatus for implementing the present invention using steady-state polarization or anisotropy measurements. POL1 and POL2 are polarizers.

FIG. 1 shows a schematic diagram for L-format measurements of fluorescent anisotropy. In FIG. 1, POL1 and POL2 represent polarizers.

Figure 2:
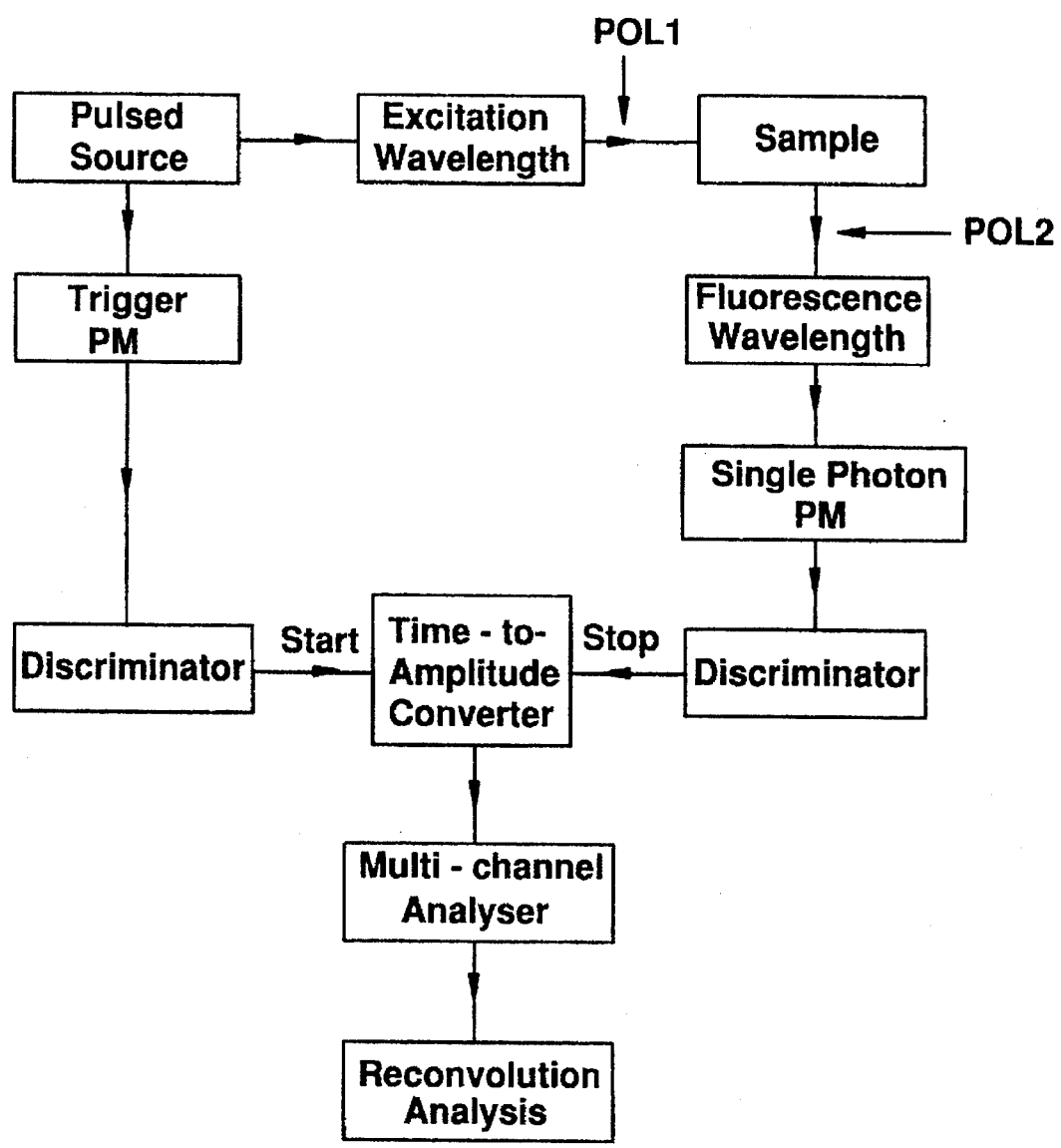
FIG. 2 is a schematic block diagram of an apparatus for implementing the present invention using time-resolved measurements.

FIG. 2 shows a typical time-correlated single-photon arrangement.

FIG. 3 illustrates how the reactive metal-ligand complexes used in the present invention can be synthesized.

Figure 4:
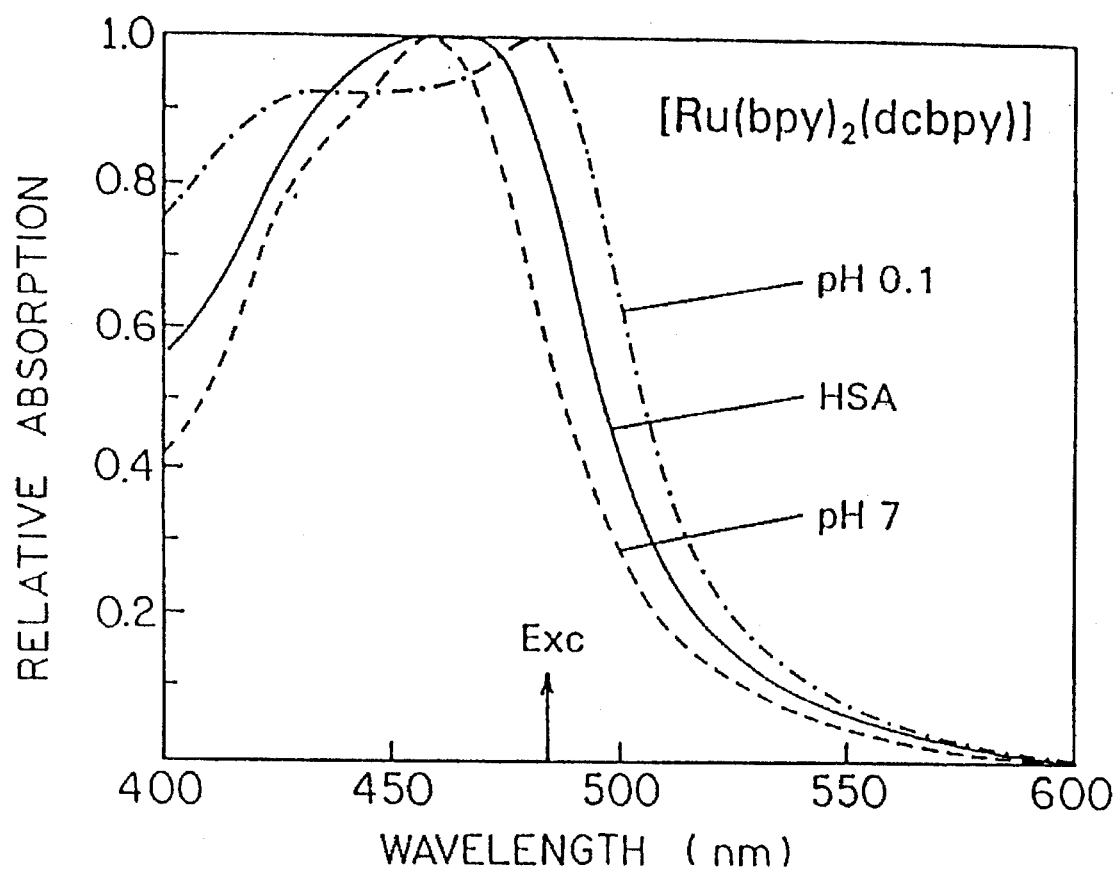
FIG. 4 shows absorption spectra of the complex when covalently bound to human serum albumin (HSA) at pH 7.0, and complex free in solution at pH 0.1 and pH 7.0. "Bpy" refers to 2,2'-bipyridine, and "dcbpy" refers to 4,4'-dicarboxy-2,2'-bipyridine.

FIG. 4 shows absorption spectra of [Ru(bpy)$_2$(dcbpy)] at pH 0.1 and 7 and when conjugated to HSA. Similar absorption spectra were found for other protein conjugates.

Figure 5:
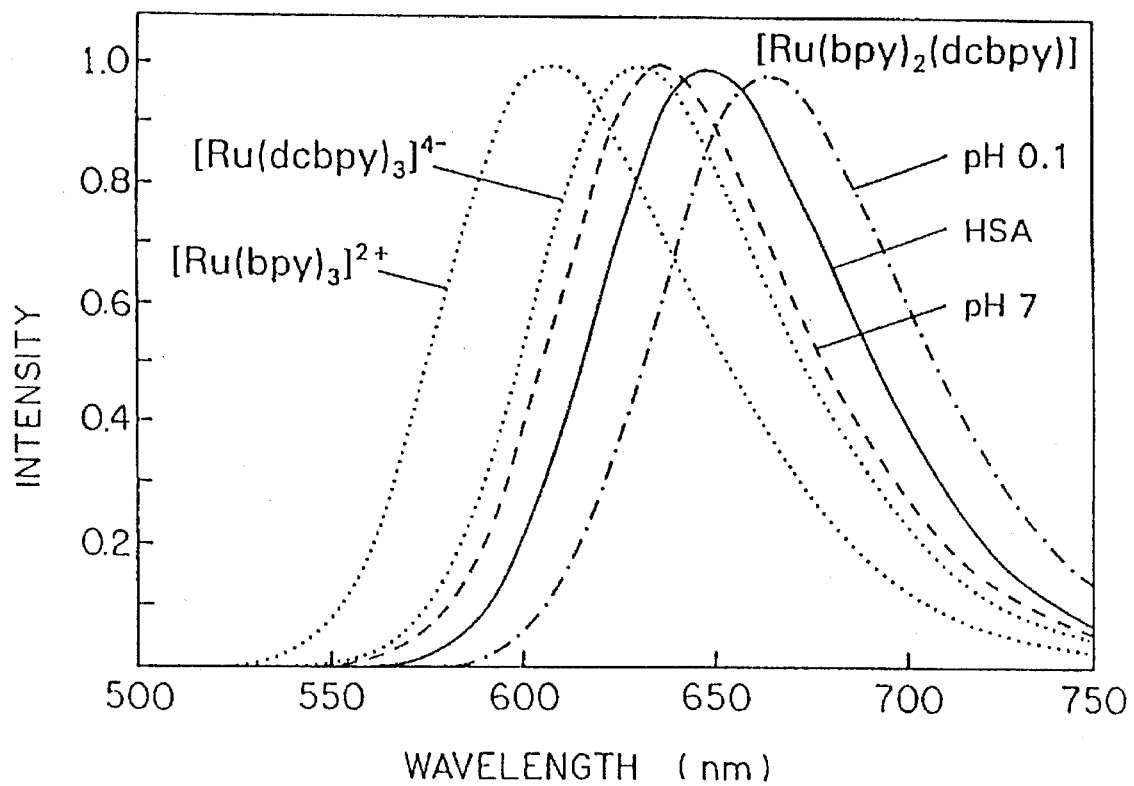
FIG. 5 shows the emission spectra of the complex free in solution (pH 0.1 and 7.0) and bound to HSA. For comparison, included are emission spectra of symmetrical Ru-complexes.

FIG. 5 shows emission spectra of [Ru(bpy)$_3$]$^{2+}$ and [Ru(dcbpy)$_3$]$^{4-}$ at pH 7.0 and [Ru(bpy)$_2$(dcbpy)] at pH 0.1 and 7 and when conjugated to HSA. Similar emission spectra were found for other protein conjugates.

Figure 6:
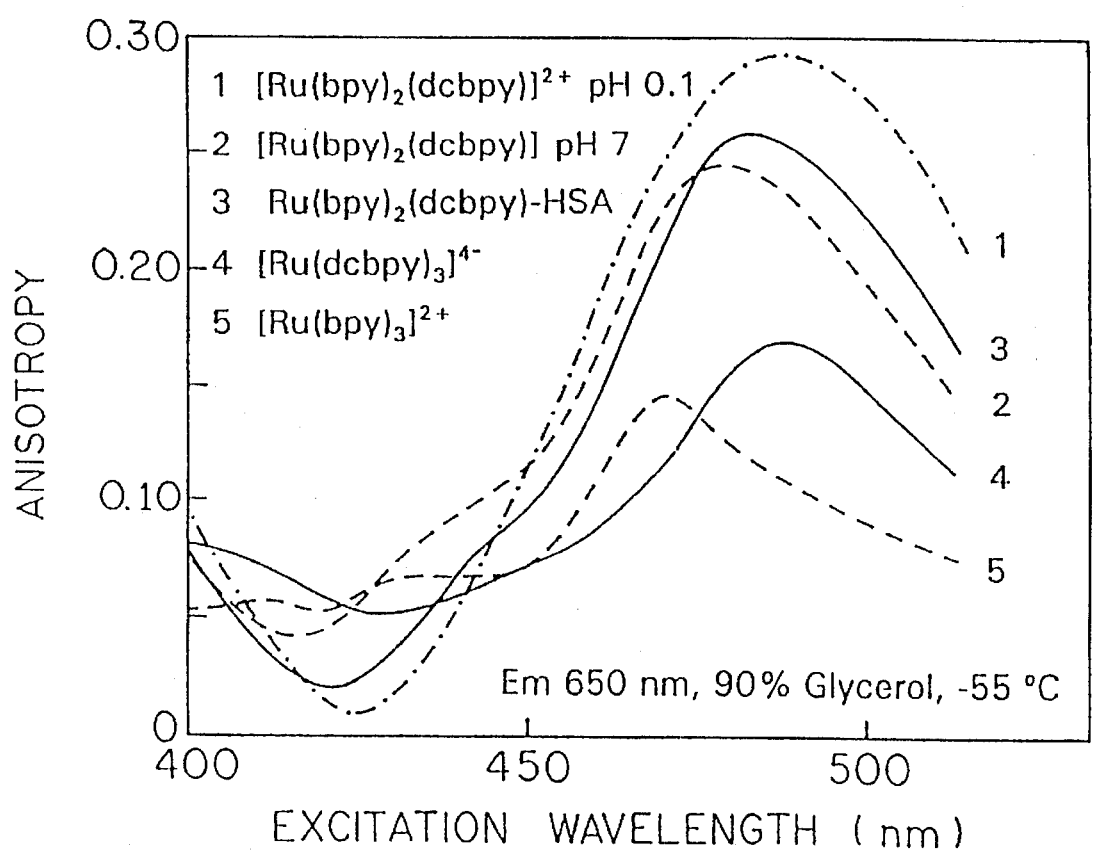
FIG. 6 shows the excitation anisotropy spectra of Ru(bpy)$_2$(dcbpy) free and bound to HSA in glycerol/water (9:, v/v) at $-55°$ C. Also included for comparison are the anisotropy spectra of the symmetrical Ru-complexes Ru(bpy)$_3^{2+}$ and Ru(dcbpy)$_3^{4-}$.

FIG. 6 shows excitation anisotropy spectra of metal-ligand complexes in glycerol/water (9:1, v/v) at −55° C. FIG. 6 shows that in frozen solutions, where rotational motion does not occur, the anisotropy of the invention complex is higher than for a symmetric [Ru(bpy)$_3$]$^{2+}$ and [Ru(dcbpy)$_3$]$^{4-}$ complexes.

Figure 7:
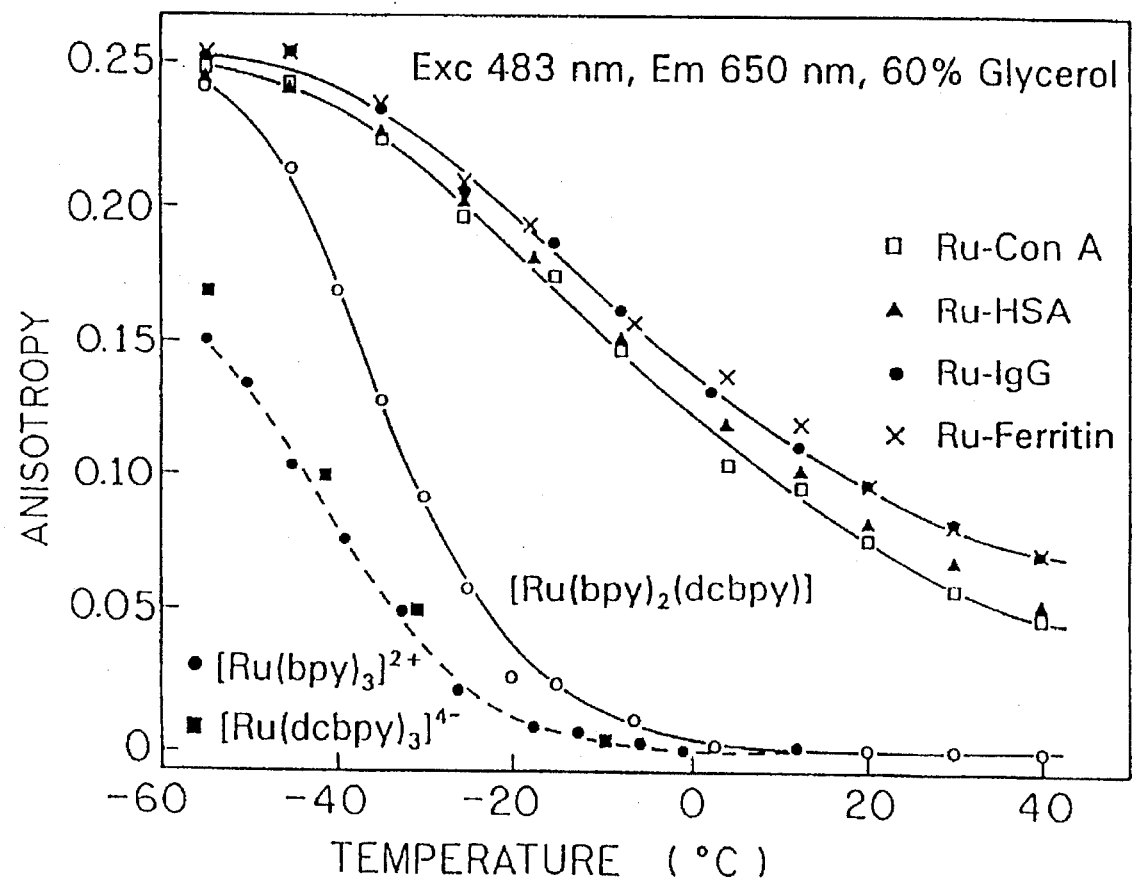
FIG. 7 shows the temperature-dependent emission anisotropy of the complex free and protein conjugates in glycerol/water (6:1, v/v). The emission wavelength for [Ru(bpy)$_3$]$^{2+}$ was 600 nm, and 650 nm for the Ru(bpy)$_2$(dcbpy) and Ru-labeled proteins.

FIG. 7 illustrates the temperature-dependent emission anisotropy of metal-ligand complexes and protein conjugates. The emission wavelength for [Ru(bpy)$_3$]$^{2+}$ was 600 nm. FIG. 7 shows that the anisotropy of Ru(bpy)$_2$(dcbpy) is higher when bound to proteins, which indicates the anisotropy will depend on the molecular weight.

Figure 8:
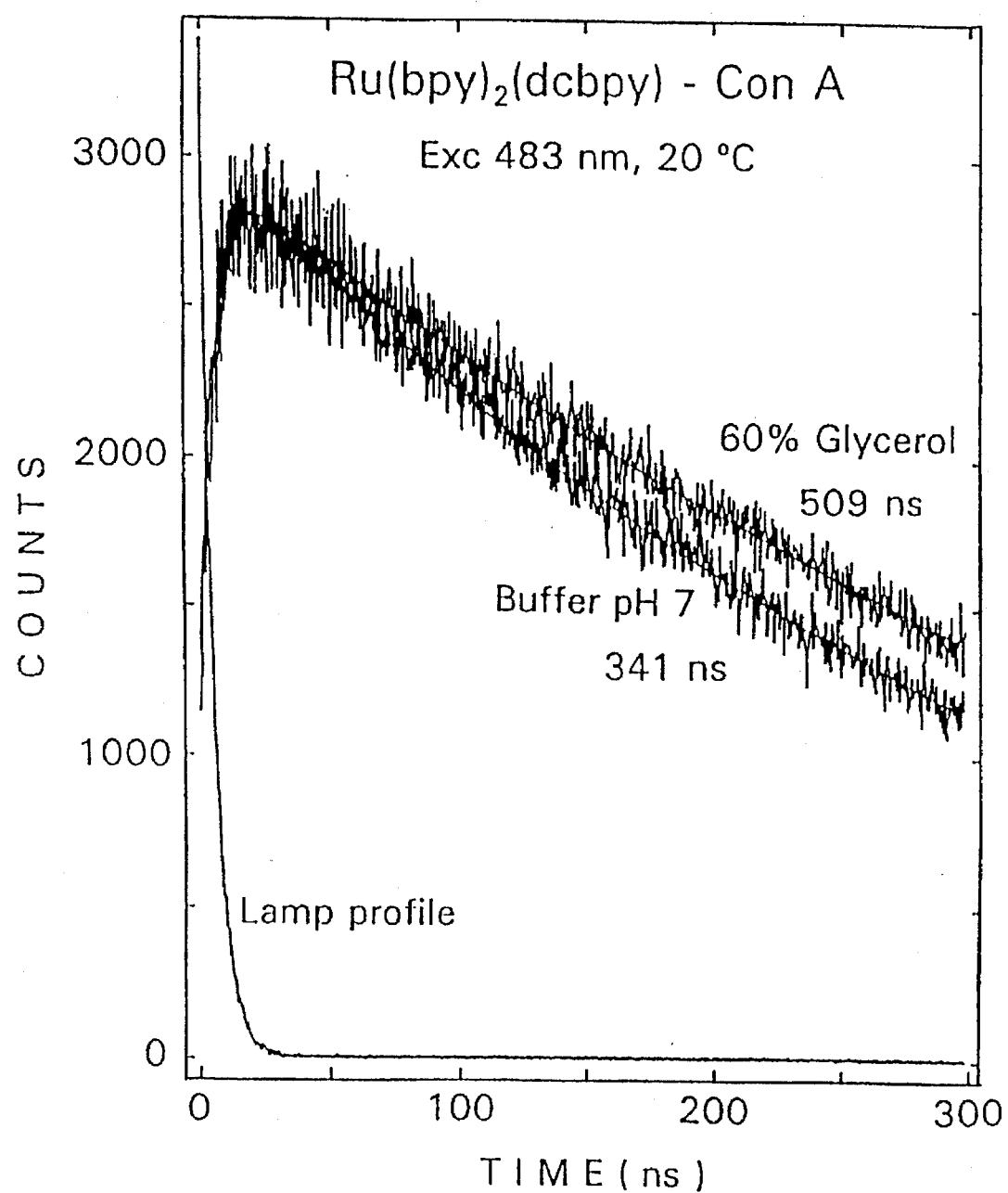
FIG. 8 shows the intensity decays of [Ru(bpy)$_2$(dcbpy)] conjugated to ConA (Concanavalin A). Similar intensity decays were obtained for [Ru(bpy)$_2$(dcbpy)] free and conjugated to other proteins. These data were obtained using an apparatus similar to that shown in FIG. 2.

FIG. 8 illustrates the intensity decays of [Ru(bpy)$_2$(dcbpy)] conjugated to ConA. Similar intensity decays were obtained for [Ru(bpy)$_2$(dcbpy)] conjugated to other proteins. FIG. 8 shows that the lifetime of the complex when bound to a protein (Concanavalin A) is near 400 ns, and thus is suitable for use in FPI of high molecular weight antigens.

Figure 9:
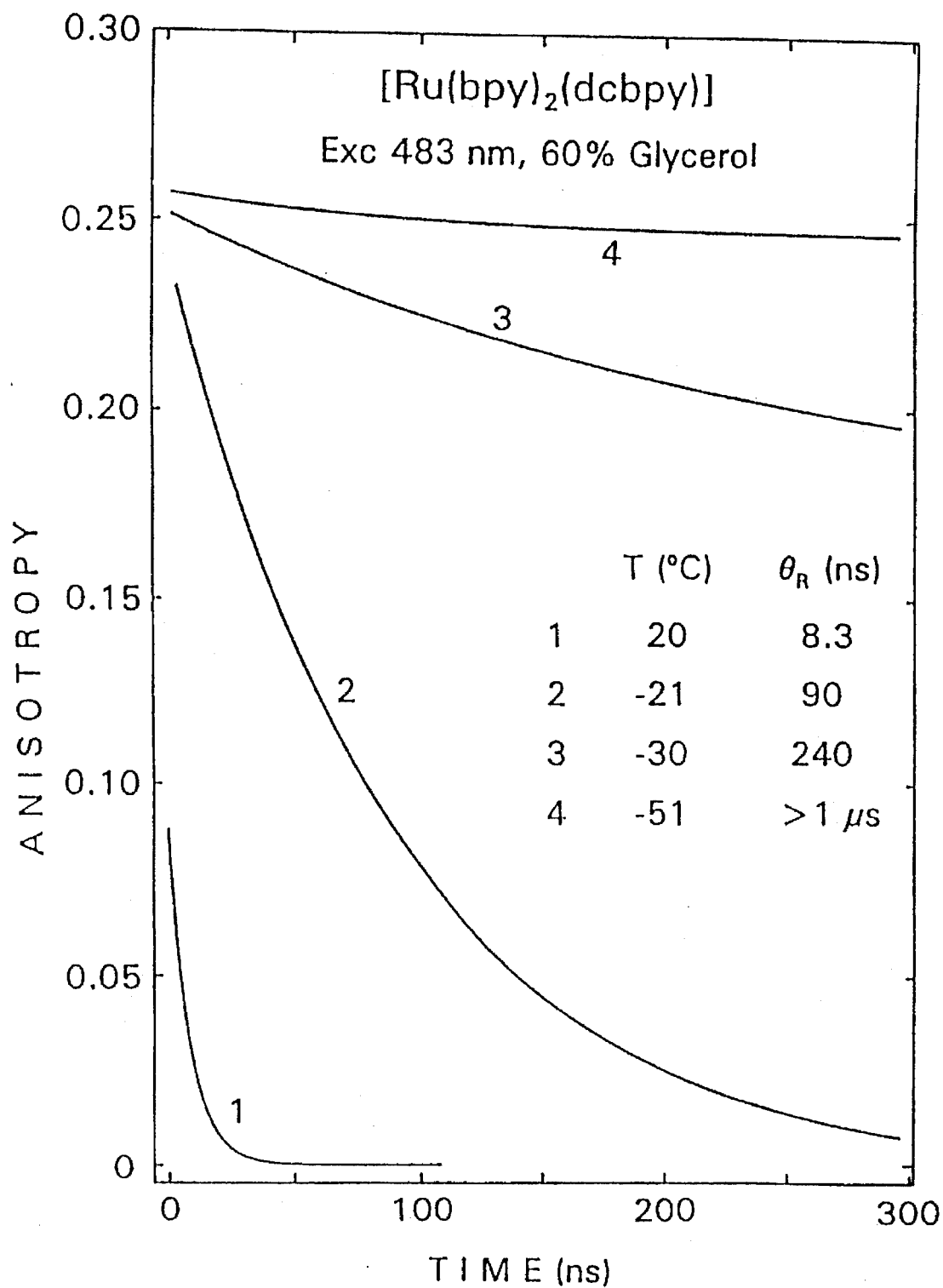
FIG. 9 shows the anisotropy decays of free [Ru(bpy)$_2$(dcbpy)] in glycerol/water (60/40, v/v) at the indicated temperatures, obtained using an apparatus similar to that shown in FIG. 2.

FIG. 9 illustrates anisotropy decays of free [Ru(bpy)$_2$(dcbpy)] in glycerol/water (60/40, v/v) at various temperatures indicated thereon. FIG. 9 shows that the anisotropy decay of the complex depends on the rotational rate of the probe, as needed for FPI.

Figure 10:
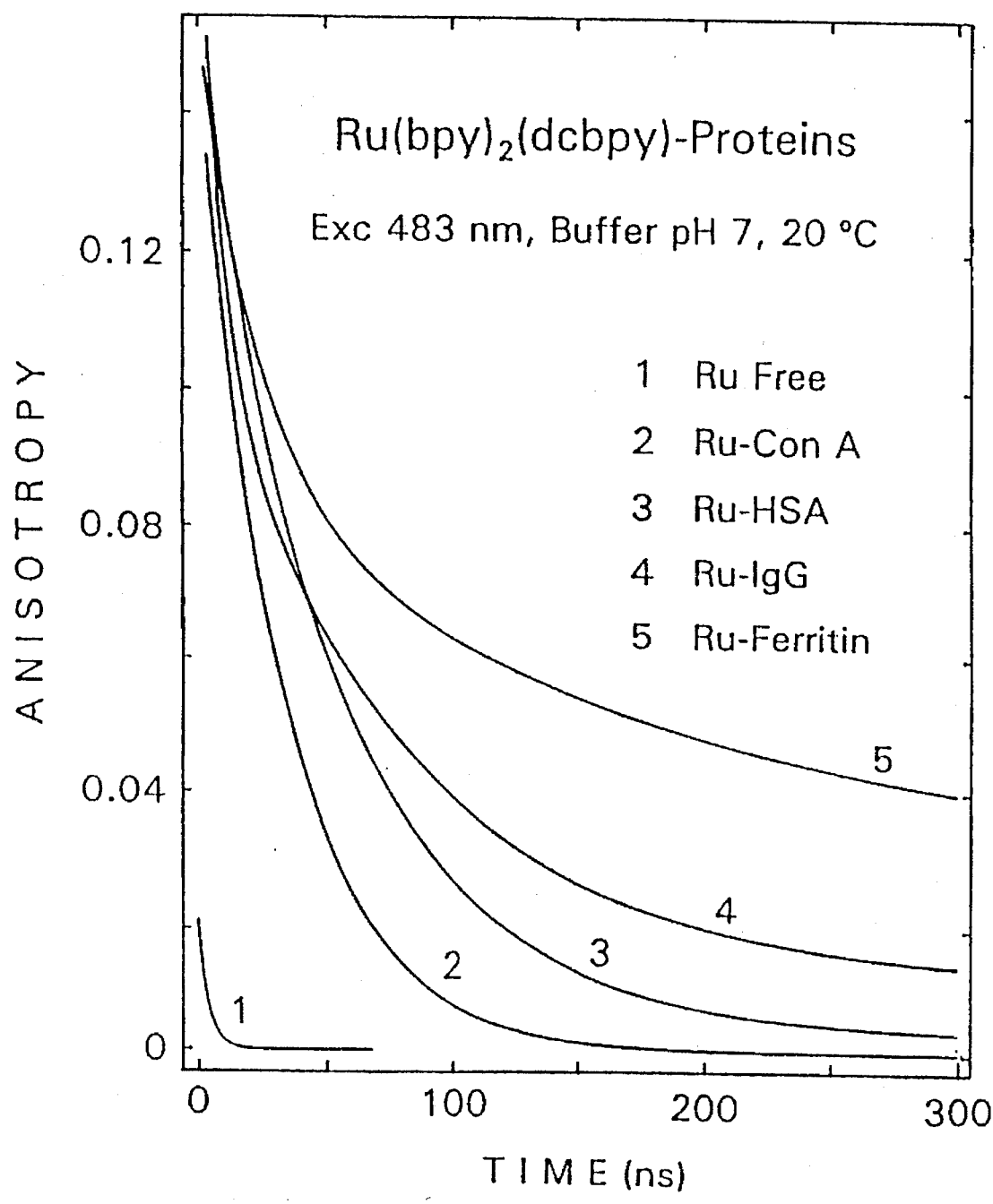
FIG. 10 shows the anisotropy decays of [Ru(bpy)$_2$(dcbpy)]free and conjugated to proteins in a buffer. The anisotropy decay is seen to be slower for higher molecular weight proteins.

FIG. 10 illustrates anisotropy decays of [Ru(bpy)$_2$(dcbpy)] in a buffer, and FIG. 10 shows that the anisotropy of [Ru(bpy)$_2$(dcbpy)] decays more slowly with higher molecular weight proteins. This sensitivity to molecular weight is essential for use in FPI.

Figure 11B:
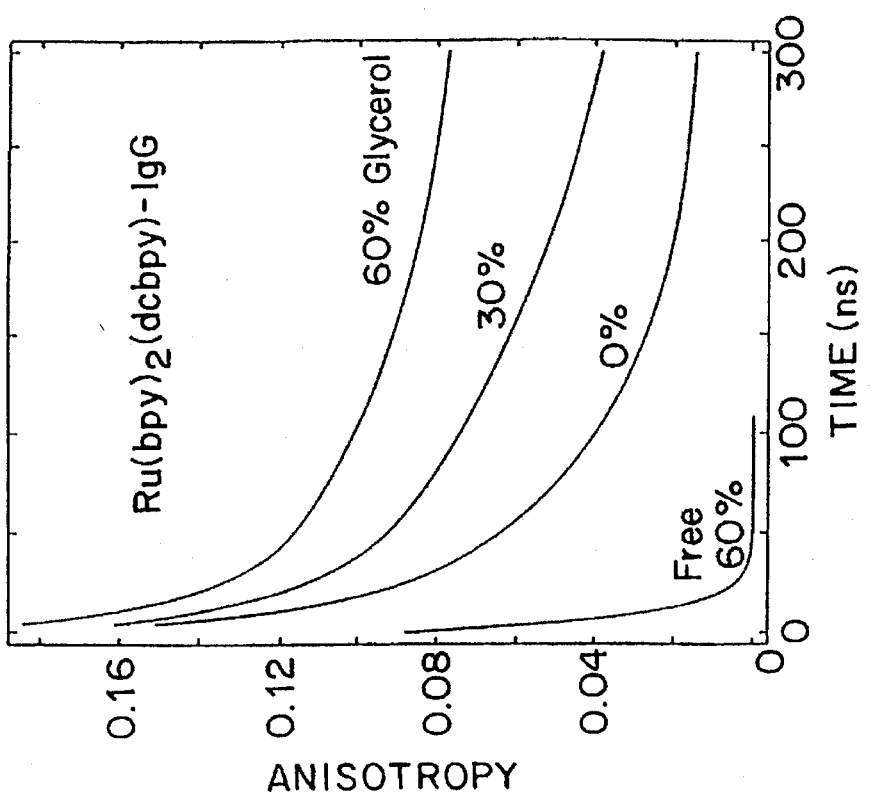
FIGS. 11A and 11B show the viscosity-dependent anisotropy decays of [Ru(bpy)$_2$(dcbpy)] conjugated to ConA and IgG, respectively. Increasing viscosity, or increasing % glycerol, results in slower anisotropy decays.
Figure 11A:
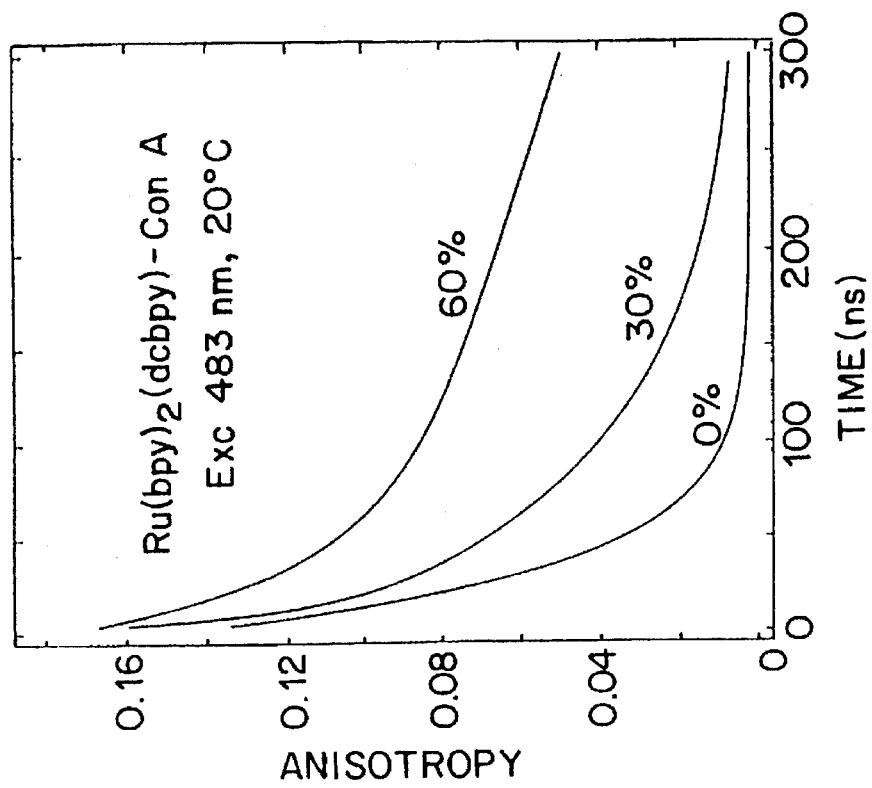

FIGS. 11A and 11B illustrate viscosity-dependent anisotropy decays of [Ru(bpy)$_2$(dcbpy)] conjugated to ConA and IgG, respectively. FIGS. 11A and 11B show that the anisotropy decays more slowly upon increasing viscosity by adding glycerol. This result again shows that the anisotropy of the complex depends on rotational rate and thus molecular weight.

Figure 12B:
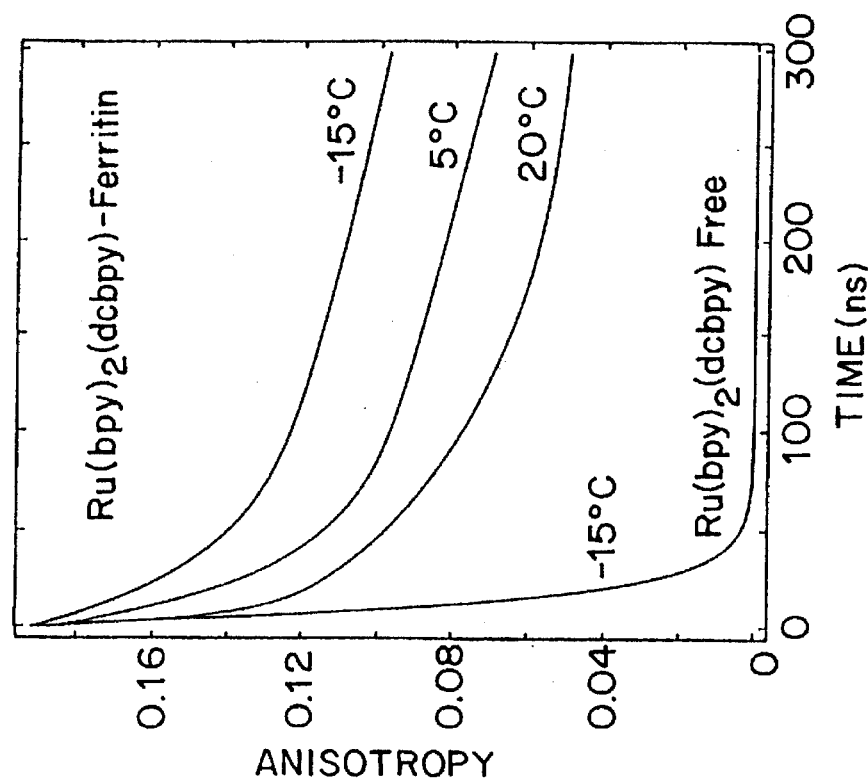
FIGS. 12A and 12B show the temperature-dependent anisotropy decays of [Ru(bpy)$_2$(dcbpy)] conjugated to HSA and Ferritin, respectively. The anisotropy decays more slowly at lower temperatures due to slower rotational diffusion.
Figure 12A:
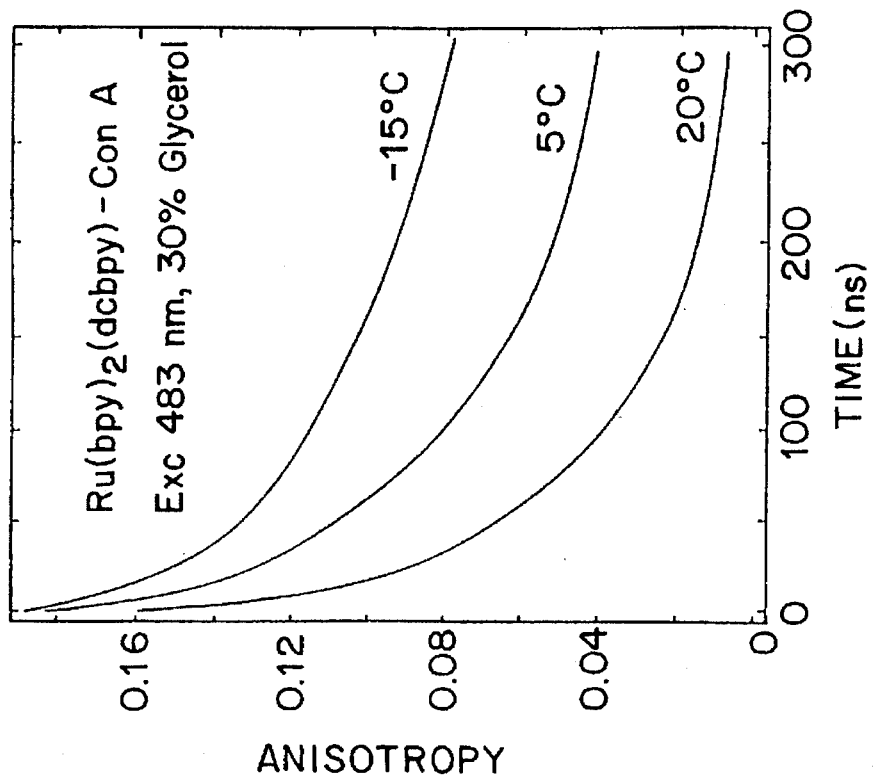

FIGS. 12A and 12B illustrate temperature-dependent anisotropy decays of [Ru(bpy)$_2$(dcbpy)] conjugated to HSA and Ferritin, respectively. FIGS. 12A and 12B again demonstrate that anisotropy decays more slowly as the rotational rate decreases, in this case by decreasing the temperature.

Figure 13:
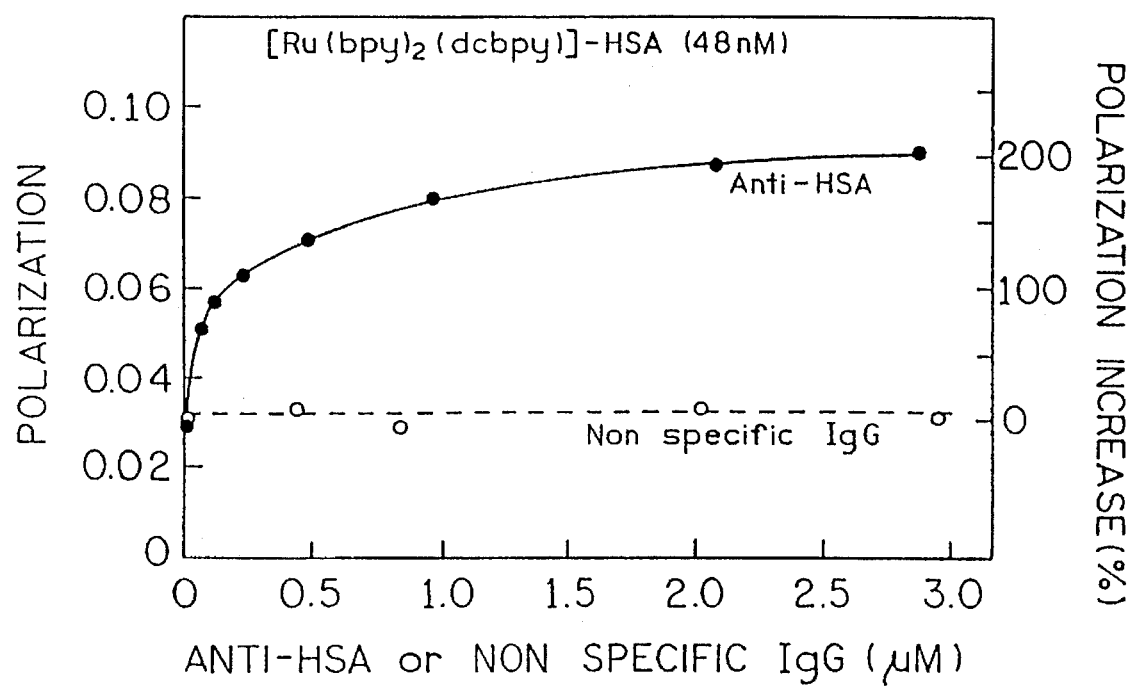
FIG. 13 shows the fluorescence polarization immunoassay of HSA.

FIG. 13 illustrates a fluorescence polarization immunoassay of HSA using the [Ru(bpy)$_2$(dcbpy)] complex with the addition of HSA-specific antibody (closed circles) and with the addition of nonspecific antibody (open circles). A significant increase in polarization is observed upon binding of HSA labeled complex to anti-HSA.

Figure 14:
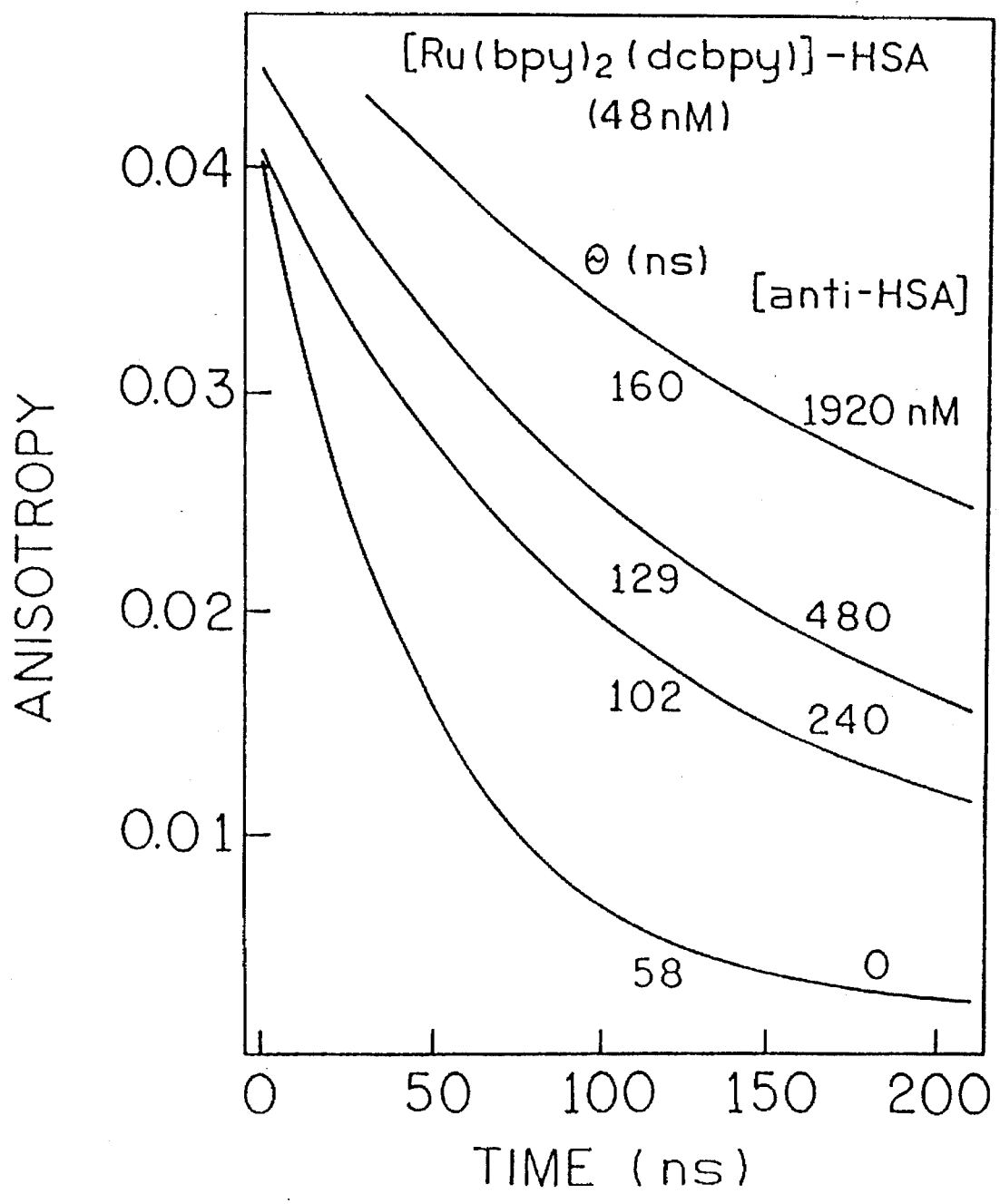
FIG. 14 shows the time-resolved anisotropy decays of the complex conjugated to HSA, in the absence and presence of various concentrations of HSA-specific antibody.

FIG. 14 illustrates the time-resolved anisotropy decays of the complex conjugated to HSA, in the absence and presence of HSA-specific antibody. It is shown that the correlation decay strongly depends on amount of anti-HSA. The increase of the correlation time observed from anisotropy decays confirms the increase of polarization observed in FIG. 13.

Figure 15:
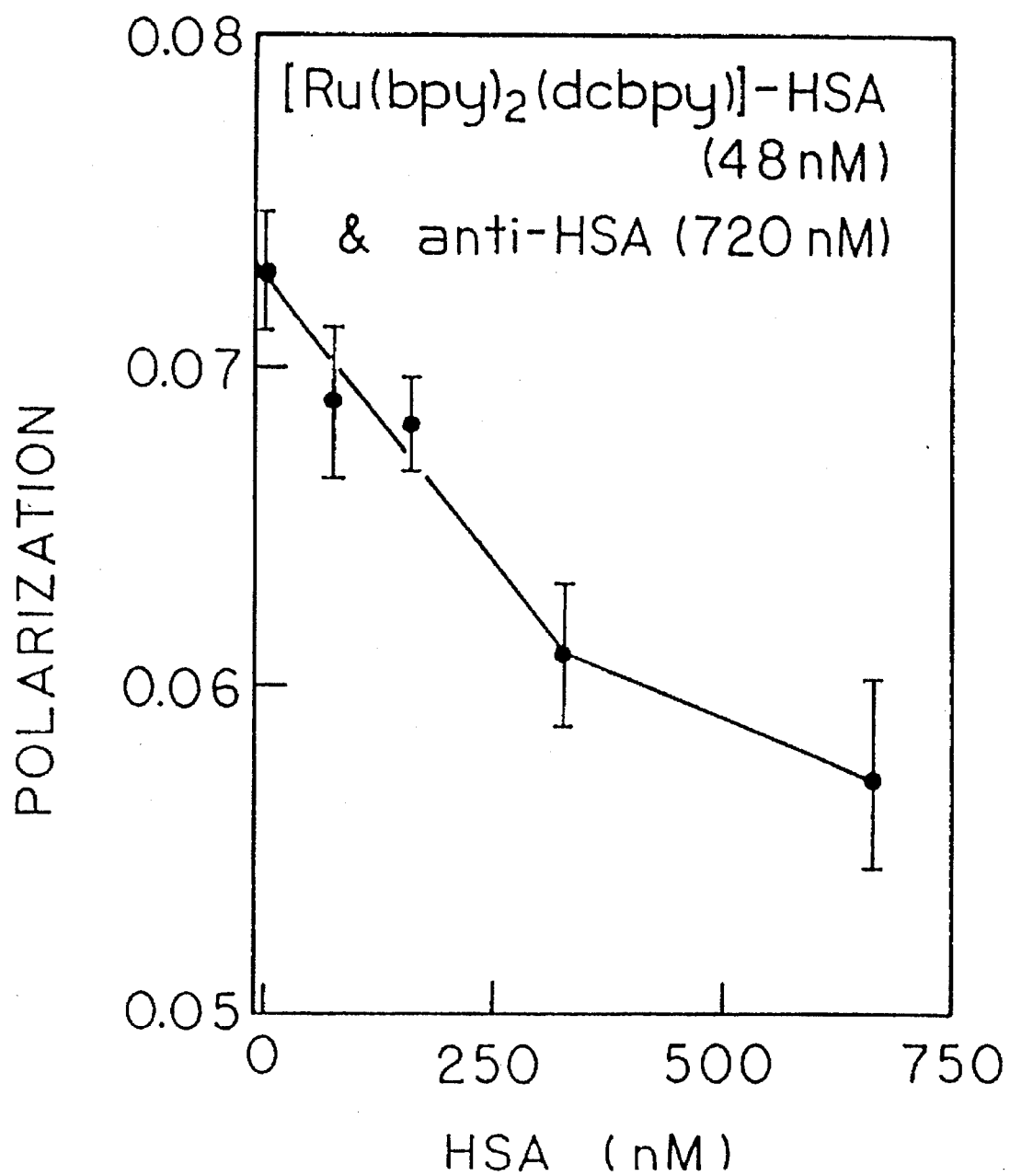
FIG. 15 shows a competitive immunoassay for HSA. In this case the presence of unlabeled HSA in the sample decreases the fluorescence polarization observed for the mixture of labeled HSA and antibody.

FIG. 15 illustrates a competitive immunoassay for HSA. In this case the presence of unlabeled HSA in the sample decreases the fluorescence polarization observed for the mixture of labeled HSA and antibody. The decrease in polarization is due to competitive binding of labeled HSA and unlabeled HSA to anti-HSA.

Figure 16:
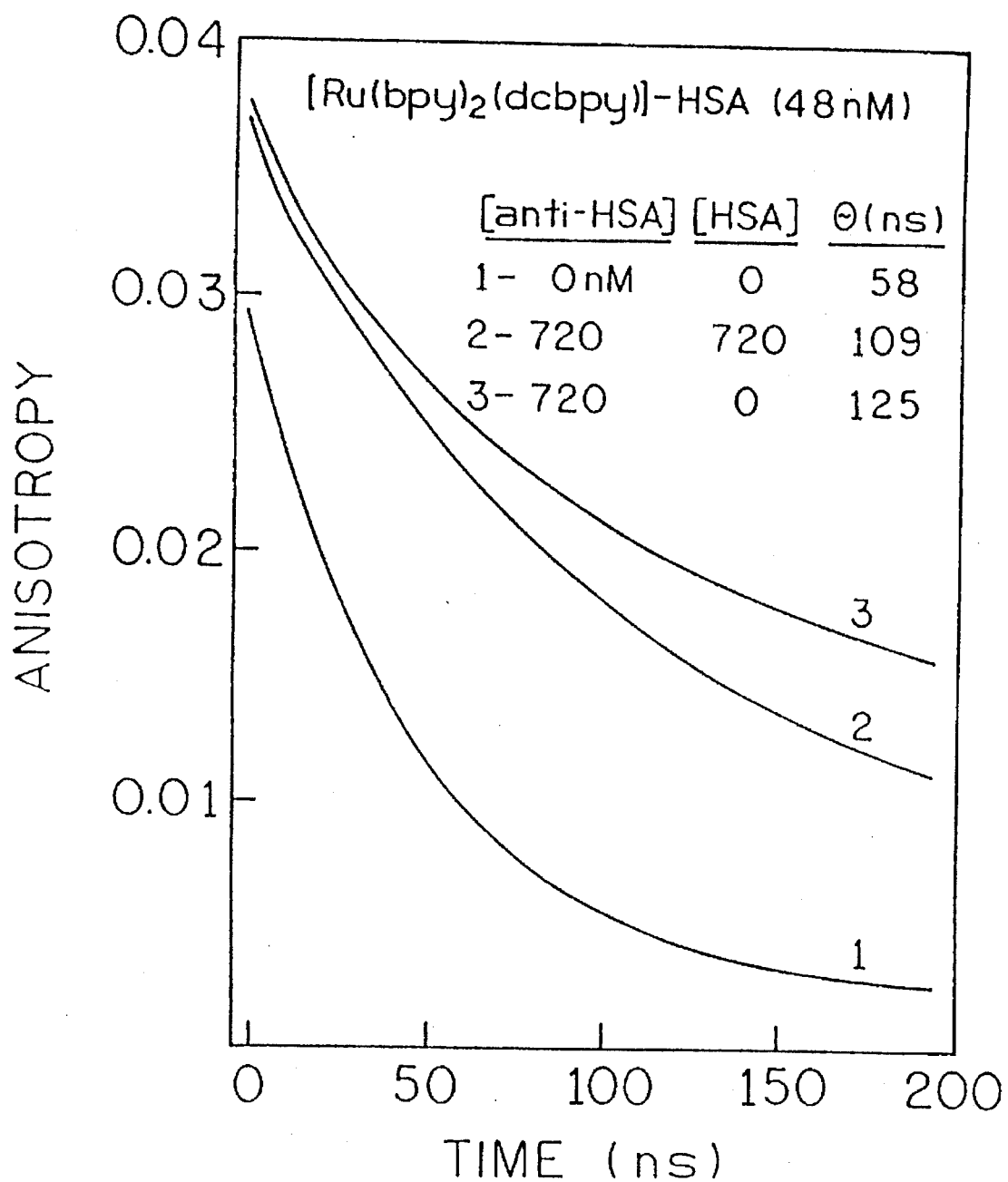
FIG. 16 shows the anisotropy decays of labeled HSA in the absence and presence of antibody, and with unlabeled HSA. The anisotropy decays more rapidly with larger concentrations of unlabeled HSA in this competitive immunoassay, which is consistent with data presented in FIG. 15.

FIG. 16 illustrates the anisotropy decays of labeled HSA in the absence and presence of antibody, and with unlabeled HSA. The anisotropy decays more rapidly with larger concentrations of unlabeled HSA in this competitive immunoassay, which is consistent with data presented in FIG. 15.

Figure 17:
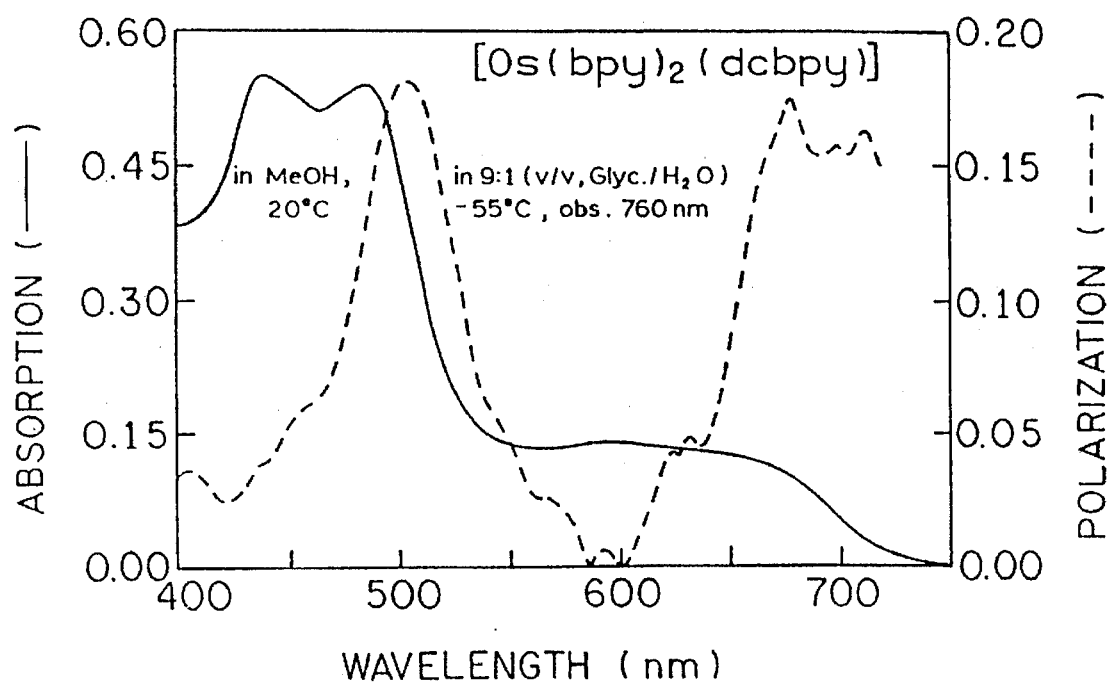
FIG. 17 shows the absorption and anisotropy spectrum of an Os complex, Os(bpy)$_2$(dcbpy).

FIG. 17 illustrates the absorption and anisotropy spectrum of an Os complex, Os(bpy)$_2$(dcbpy). This complex displays high anisotropy in frozen solution. This indicates that this compound can also be useful as a probe of protein rotation, i.e., affinity assays.

Figure 18:
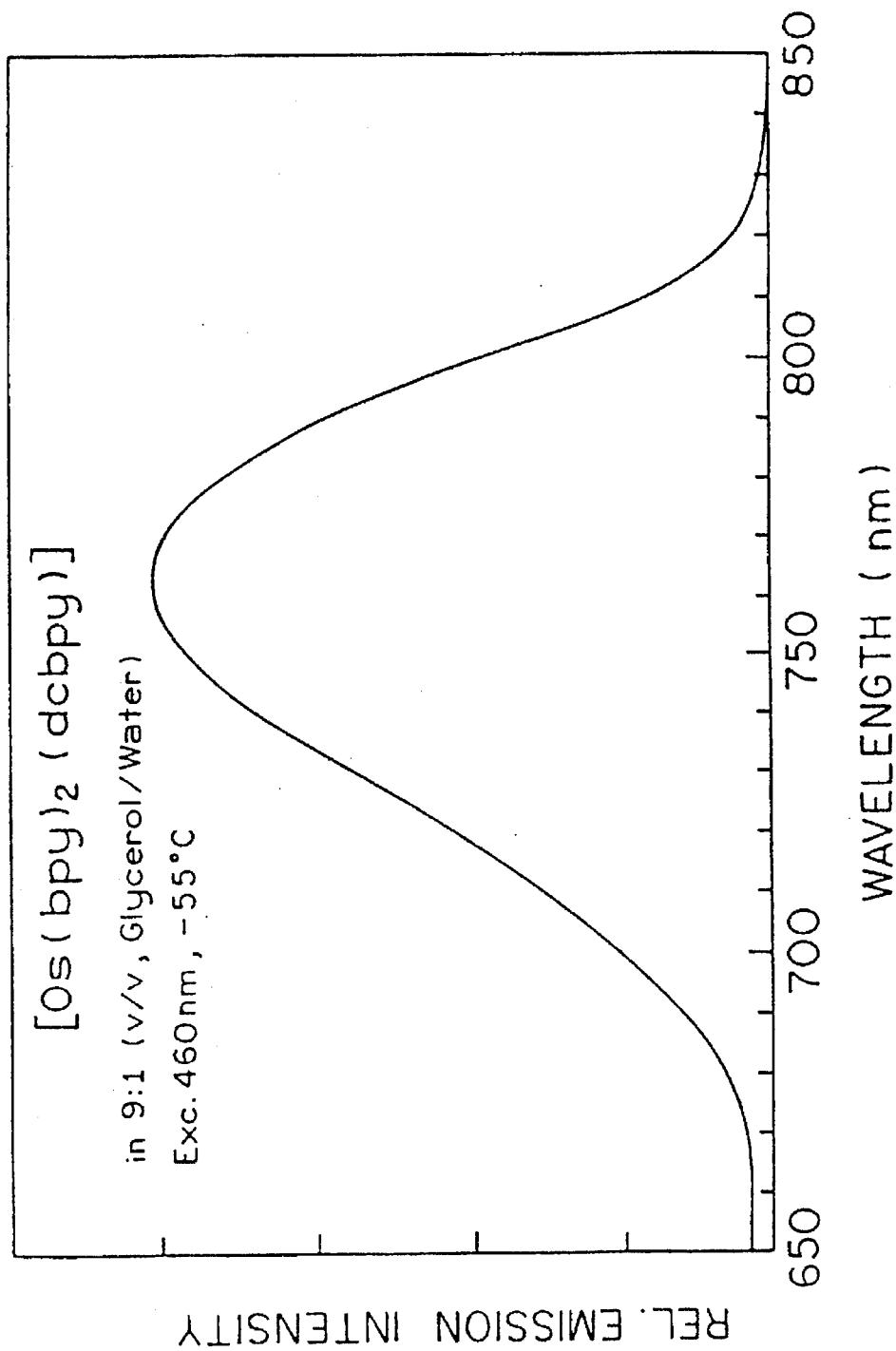
FIG. 18 shows the emission spectrum of the Os complex.

FIG. 18 illustrates the emission spectrum of the Os complex.

An important characteristic of the Os complex is its long wavelength absorption and emission. It can be excited with laser diodes from 600 to over 700 nm, or possibly a light emitting diode or an electroluminescent device. The extent of autoflourescence decreases at longer wavelengths.

The lifetime of the Os complex can be near 50 ns. This lifetime may be better than the Ru complex (400 ns) for substances like serum albumin (MW≈70,000) with correlation times near 50 ns. The Ru complex may be better for higher molecular weight antigens. However, it should be noted that some osmium ligand complexes are known to display longer lifetimes near 400 ns. In this case the use of osmium metal-ligand complexes will have the combined advantages of the long lifetimes described for the ruthenium metal-ligand complexes, and in addition will display long wavelength absorption and emission. The long wavelength absorption allows excitation with laser diodes and other simple light sources.

Figure 19:
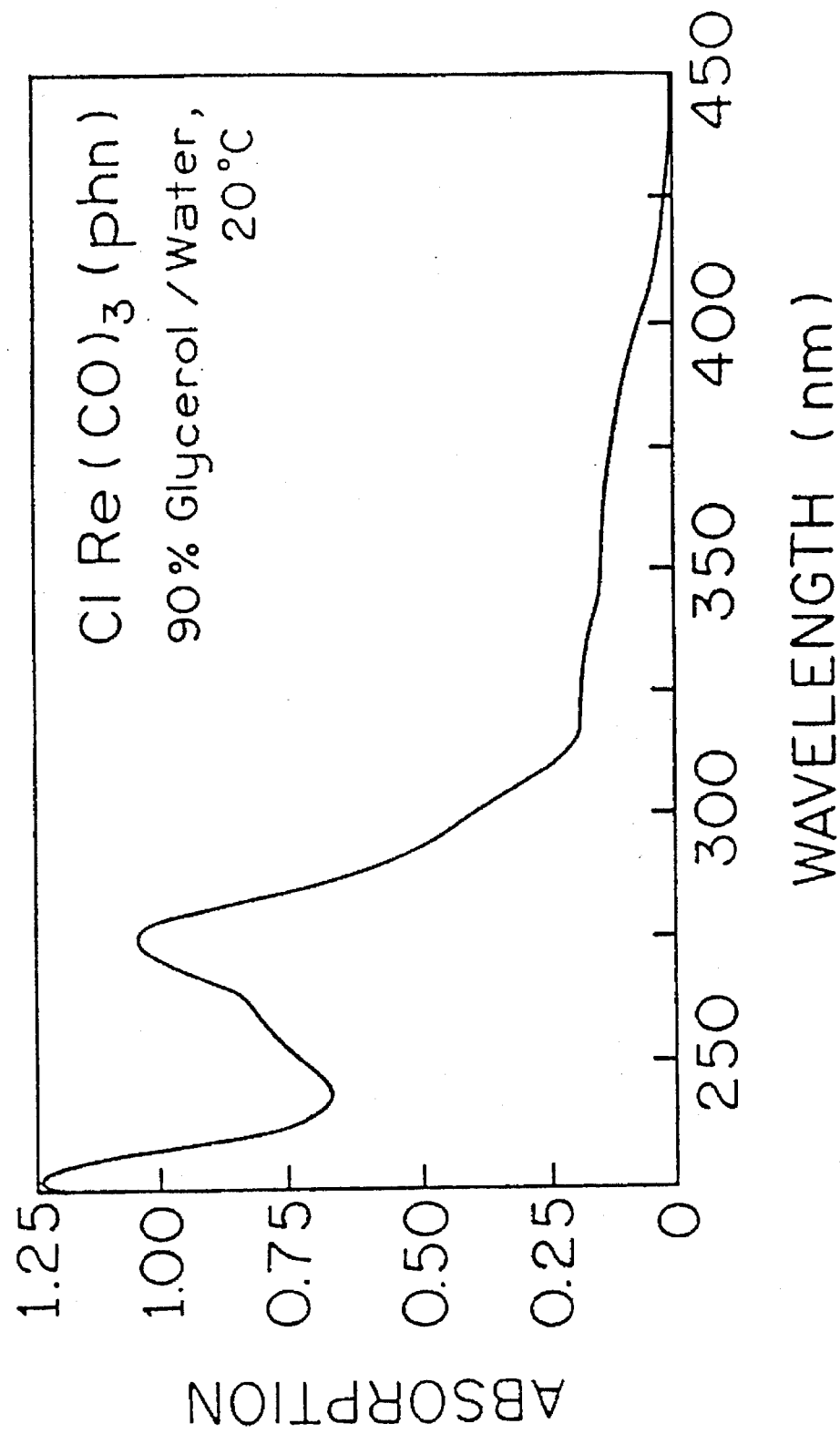
FIG. 19 shows the absorption spectrum of a Rhenium (Re) complex.
Figure 20:
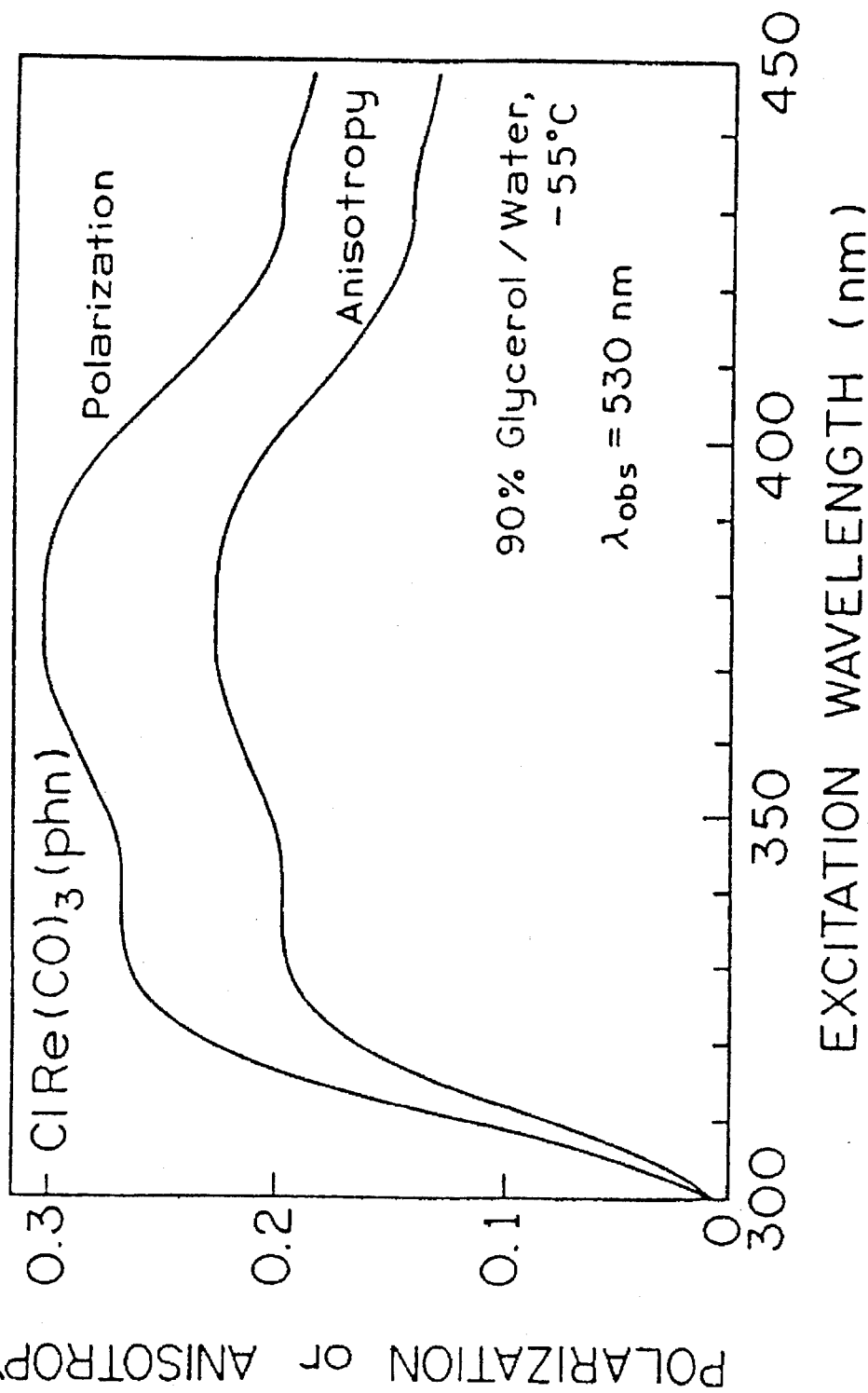
FIG. 20 shows the excitation anisotropy spectrum of a Re complex.

FIGS. 19 and 20 illustrate the absorption and anisotropy spectra of a Rhenium (Re) complex. The Re complex displays good polarization at a wide range of excitation wavelengths, and it should be useful in immunoassays and affinity assays.

Figure 21:
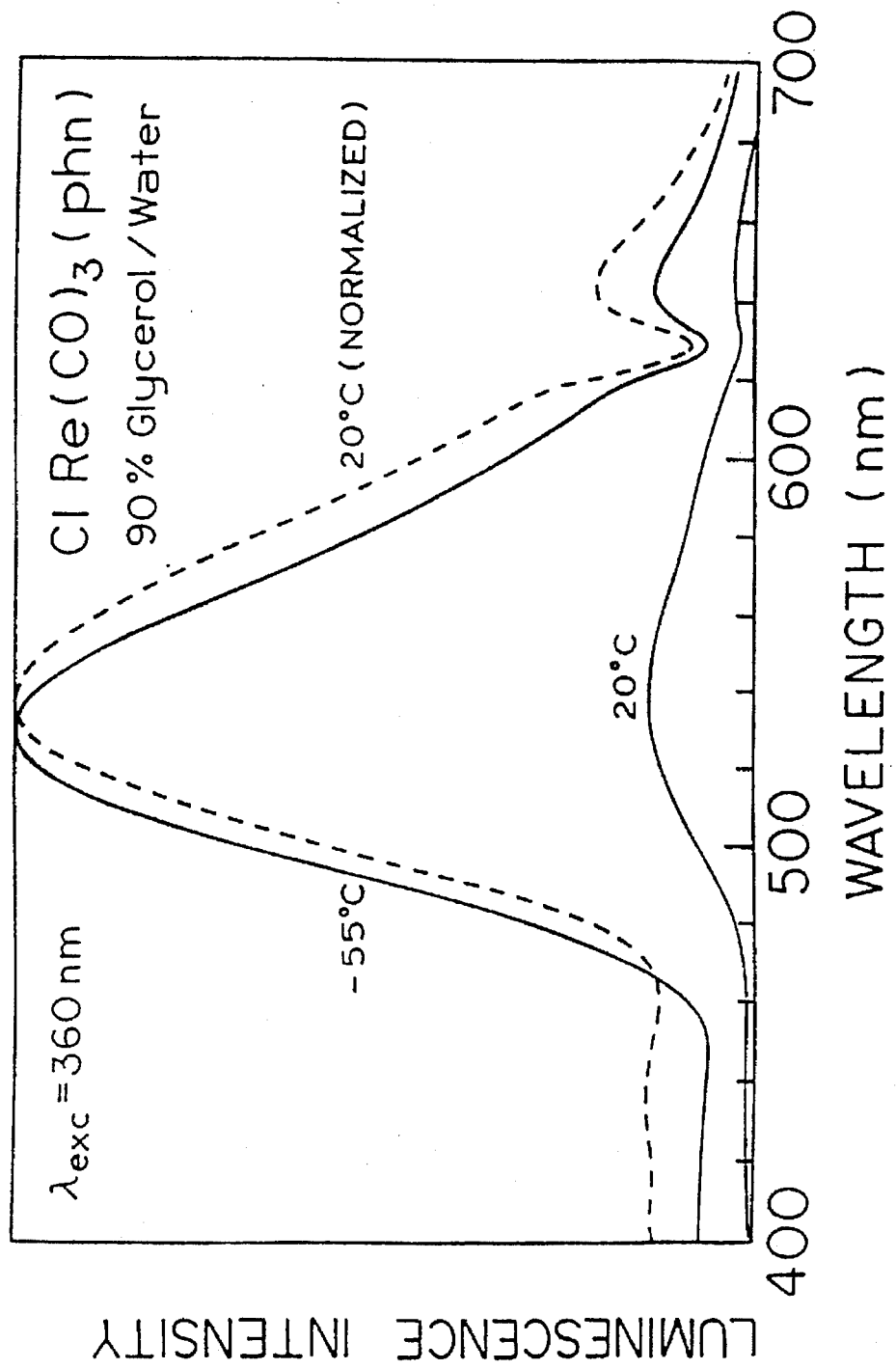
FIG. 21 shows the emission spectra of a Re complex.

FIG. 21 shows the emission spectra for an Re complex. The quantum yield and lifetime of an Re complex depend on temperature.

In a direct polarization assay of the present invention, the asymmetric metal-ligand complex can be conjugated to a receptor, antibody or lectin. A receptor, antibody or lectin can also be used in a competitive immunoassay of the present invention, i.e., as the molecule which specifically binds the analyte.

In the present invention, the sample of interest can be an antigenic substance or other analyte with a molecular weight over 2,000. The antigenic substance can be a protein, nucleic acid, polysaccharide, or combination of these substances. Also, the antigenic substance can be a cellular or cell surface antigen, glycopeptide, lipoprotein, or glycolipid, which can be naturally present or due to a foreign object (such as bacteria or a virus).

The exciting electromagnetic energy used in the present invention can be a linearly polarized light pulse, and the method can further comprise the step of measuring the polarization of the fluorescent light only after background autoflourescence of the coupled sample has subsided. The exciting step can implemented by a light source selected from the group consisting of a flash lamp, a modulated lamp, an electroluminescent device, a light-emitting diode and a laser (such as a diode laser or an amplitude modulated laser). The light pulse and the fluorescent light can be transmitted through optical fibers. The measuring step in the present invention can be performed using an implanted patch containing the coupled sample. In the method of the present invention, the steady state of linear polarized light can be dependent on a characteristic of the coupled sample or any uncoupled analyte which is present. Also, the intensity decay or polarization decay can be dependent on the coupled sample. The amount of analyte can be estimated from time-dependent anisotropy decay as measured following pulsed excitation. Also, the amount of analyte can be determined from the emission anisotropy decay measured with amplitude-modulated excitation by phase-modulation fluorometry.

In a particularly preferred embodiment of the present invention, the immunoassay is a competitive immunoassay.

Another preferred embodiment of the present invention is an affinity assay. In the affinity assay, the molecule which has affinity for the analyte can be selected from the group consisting of strepavidin, avidin, biotin, and lectins. A desirable type of affinity assay uses proteins (e.g., proteins which bind glucose and polysaccharides, like Concanavalin A).

The invention can also be used in affinity assays based on specific binding between macromolecules. For instance, Concanavalin A has affinity for dextran, and is displaced by glucose. The polarization of a mixture of labeled Con A and dextran can be expected to display polarization values which depend on glucose concentration.

The present invention will now be described in further detail by way of the following experimentation. Unless otherwise indicated, all parts, percents, ratios and the like are by weight.

EXPERIMENTATION

MATERIALS AND METHODS $RuCl_3$, $Ru(bpy)_2Cl_2$ and $Ru(bpy)_3Cl_2$ were purchased from the Aldrich Chemical Company. Chemical synthesis of the NHS-ester of $[Ru(bpy)_2(dcbpy)]^{2+}$ and of the more symmetric complex $[Ru(dcbpy)_3]^{2+}$ was carried out as described in FIG. 3.

Synthesis of Rubis(2,2'-bipyridine)(2,2'-bipyridine-4,4'-dicarboxylic acid) bis(hexafluorophosphate) (1): $Ru(bpy)_2Cl_2$ (0.4 g), $NaHCO_3$ (0.4 g) and 2,2'-bipyridine-4,4'-dicarboxylic acid (0.3 g) were heated in $MeOH:H_2O=4:1$ for 8 to 10 hours. The solution was cooled in an ice bath for 2 hours, and the pH was adjusted with concentrated $H_2SO_4$ to 4.4 . The formed precipitate was filtered and then washed with MeOH, the filtrate was treated with 5 g $NaPF_6$ in 25 ml $H_2O$ and then cooled in an ice bath, and the precipitate was collected by filtration. Yield: 0.6 g (77%).

Synthesis of Ru tris(2,2'-bipyridine-4,4'-dicarboxylic acid) bis (hexafluorophosphate) (2): $RuCl_3$ (0.1 g) and 2,2'-bipyridine-4,4'-dicarboxylic acid (3.67 g) were suspended in 15 ml ethylene glycol and refluxed for 2 hours. The solution was cooled to room temperature and filtered. After the addition of 2.5 g $NaPF_6$ in 25 ml $H_2O$, the pH of the filtrate was adjusted to 1.0 with concentrated $H_2SO_4$, and the solution was cooled for a few hours. The precipitate was collected and resuspended in MeOH, filtered and dried over $P_4O_{10}$. Yield: 0.38 g (68%).

Synthesis of the NHS esters: Ru tris(2,2'-bipyridine-4,4'-dicarboxylic acid) N-hydroxysuccinimide ester (4). 0.46 g DCC and 0.238 g N-hydroxysuccinimide were dissolved in 3 ml DMF with stirring and cooled in an ice bath. A solution of 0.38 g Ru tris(2,2'-bipyridine-4,4'-dicarboxylic acid) (2) was added, and the mixture stirred for a few hours. The formed precipitate was removed by filtration through a syringe filter, and the filtrate containing the active Ru-complex was used for labeling the substrates.

The proteins HSA, IgG, ConA and Ferritin were obtained from Sigma Chemical Company and used without further purification. The proteins (10 mg portions) were labeled by adding a 100-fold molar excess of the Ru-NHS ester in 50 µl of DMF to 1 ml of stirred protein solution (0.2M carbonate buffer, pH 8.3–9.1), followed by a 2–6 hour incubation and purification of the labeled protein by gel filtration chromatography on Sephadex G-25 or G-50, using 0.1M PBS, pH 7.2.

Fluorescence intensity and anisotropy decays were measured by time-correlated single photon counting (TCSPC). The primary light source was a cavity-dumped (1 MHz) pyridine 1 dye laser, with the frequency doubled to 360 nm. This dye laser was pumped by a mode-locked Nd:YAG laser. The 360 nm output was less useful for excitation of the Ru-complex because of the lower anisotropy at this excitation wavelength. Hence, the 360 nm laser pulses were generally used to illuminate a nearly saturated solution of perylene in cyclohexane and a 483 nm interference filter to isolate the perylene emission, which was used to excite the Ru-complexes. The approximate 5 ns decay time of the "lamp" was easily short enough for the 200–500 ns decay times displayed by the invention samples. Detection of the emission was accomplished with a Hammamatsu R2809 microchannel plate (MCP) PMT and the usual electronics for TCSPC. Some of the time-resolved intensity decays (FIGS. 14 and 16) were obtained using 360 nm excitation.

The time-resolved intensity decays (I(t)) were fit to the single and double exponential models, $$I(t) = \sum_{i=1}^{2} \alpha_i \exp(-t/\tau_i) \quad (9)$$

where $\alpha_i$ are the pre-exponential factors and $\tau_i$ are the decay times using software from IBH Software (Edinburgh, Scotland). The "lamp" function was taken as the response observed from a scattering solution at 483 nm illustrated with the perylene "lamp".

The time-resolved anisotropy decays were obtained by measuring the time-dependent decays of the vertically ($I_\parallel(t)$) and horizontally ($I_\perp(t)$) components of the emission:

$$r(t) = \frac{I_\parallel(t) - I_\perp(t)}{I_\parallel(t) + 2I_\perp(t)} \quad (10)$$

These data were fit to a single and double correlation time model, again using standard software.

$$r(t) = \sum_{i=1}^{2} r_{0i} \exp(-t/\theta_i) \quad (11)$$

where $r_{0i}$ are the amplitudes and $\theta_i$ are the rotational correlation times.

Steady-state fluorescence data were obtained using a spectrofluorometer from SLM Instruments, with magic-angle polarizer conditions and a Hamamatsu R-928 detector. The emission spectra are uncorrected.

RESULTS

Absorption spectra of [Ru(bpy)$_2$(dcbpy)], here called the Ru-complex, are shown in FIG. 4. These spectra are normalized to unity to facilitate comparison. The absorption spectra of the Ru-complex depends on pH. At pH 7, the net charge on the complex is expected to be zero, with two positive charges on the Ru and two negative charges from the two dcbpy ligands. The long-wavelength absorption spectra of the Ru-labeled proteins are similar, and appear to be intermediate to that observed for the Ru-complex at pH 7 and 0.1. These absorption wavelengths allow excitation using simple blue LED, blue electroluminescent light sources, or frequency-doubled laser diodes.

Emission spectra of [Ru(bpy)$_2$(dcbpy)] in aqueous solution are shown in FIG. 5. The emission spectrum of the Ru-complex at pH 7.0 is comparable to that observed for [Ru(dcbpy)$_3$]$^{4-}$ with a small red-shift (5 nm) and significantly red shifted relative to [Ru(bpy)$_3$]$^{2+}$ by 28 nm. This suggests that the spectral properties of the Ru-complex are determined by the presence of a single dcbpy ligand. Consequently, the anisotropy of [Ru(bpy)$_2$(dcbpy)] may be higher than that of more symmetrical complexes, because the excited state may be localized between the metal and a single ligand, rather than being delocalized among the three ligands. The emission spectra of the Ru-labeled proteins are similar and also appear to be intermediate to that observed for Ru-complex at pH 7 and 0.1 (see FIG. 5). Similar spectra and quantum yields were found for all the labeled proteins. A somewhat lower quantum yield was found for labeled Ferritin, which is probably due to the long wavelength absorption of Ferritin and the possibility of Förster and/or Dexter transfer from the Ru to the protein.

The effect of oxygen quenching on quantum yields was also investigated. In the absence of oxygen, air equilibrated and oxygen equilibrated buffer solutions, the relative fluorescent intensities were 1, 0.77, 0.44 and 1, 0.89, 0.65 for [Ru-(bpy)$_2$(dcbpy)] and Ru-HSA, respectively. While this probe is sensitive to dissolved oxygen, the sensitivity of Ru-complex-labeled proteins is modest and will not require elimination of oxygen to observe the emission.

The steady-state excitation anisotropy spectra were examined for [Ru(bpy)$_3$]$^{2+}$, [Ru(dcbpy)$_3$]$^{4-}$ and [Ru(bpy)$_2$(dcbpy)] free and labeled to HSA (see FIG. 6) in vitrified solution where rotational diffusion does not occur during the excited state lifetime. Importantly, the asymmetric complex [Ru(bpy)$_2$(dcbpy)] and its protein conjugates displayed anisotropies from 0.25 to 0.3 for excitation near 480–490 nm. In contrast, the anisotropy spectra of [Ru(bpy)$_3$]$^{2+}$ and [Ru(dcbpy)$_3$]$^{4-}$ displayed considerably smaller values at all excitation wavelengths above 450 nm. Evidently, the presence of a non-identical ligand is important for obtaining a useful anisotropy probe.

The steady-state anisotropy of the labeled proteins and of the Ru-complex was examined over a range of temperatures and/or viscosities (see FIG. 7). The solvent was 60% glycerol/40% buffer, which formed an optically clear glass at −55° C. At low temperatures (−55° C.) the anisotropies were nearly identical for the free Ru-complex and for the Ru-labeled proteins. The anisotropy values was about 0.25, which is close to 0.28 obtained at −70° C. In contrast, the steady-state anisotropies of [Ru(bpy)$_3$]$^{2+}$ and [Ru(bpy)$_3$]$^{4-}$ remained low at all temperatures.

For the Ru-complex and the Ru-labeled proteins, the temperature-dependent anisotropies indicate that the anisotropies are sensitive to rotational motions (see FIG. 7). The steady-state anisotropy of the free Ru-complex decreased rapidly above −50° C., whereas the anisotropies of the Ru-labeled proteins decreased more slowly with temperature, and remained relatively high even at 20° C. The steady-state values were only moderately dependent on the molecular weight: Ferritin=500,000, IgG=160,000; ConA=102,000; HSA=65,000 daltons. As will be shown below, some of the anisotropy of the Ru-protein complexes is lost by fast motions of the probe in addition to rotational motion of the proteins. Importantly, the anisotropies of the labeled proteins are always larger than that of the free Ru-complex (see FIG. 7), which indicates that protein hydrodynamics contributes to the anisotropy. The detection of rotational motions using these complexes is not an obvious result. A large number of published reports have suggested that the anisotropy and anisotropy decay of the Ru metal-ligand complexes is due to intermolecular processes such as randomization of the excited state among the three organic ligands and/or interactions with the solvent which result in localization of the excited state after randomization.

The time-range of anisotropy decay measurements is determined by the lifetime of the excited state. We used TCSPC to determine the luminescence lifetimes of the Ru-complex and the Ru-labeled proteins. The intensity decays were closely approximated by a single decay time (see FIG. 8). The decay times of the labeled proteins were comparable to that of the Ru-complex alone under a comparable experimental condition, as shown below in Table I.

TABLE I

Fluorescence lifetime of [Ru(bpy)$_2$(dcbpy)] and the labeled proteins.[a]

| Protein | Buffer pH 7.0, 20° C. $\tau$ (ns) | 60% glycerol 20° C. $\tau$ (ns) | 30% glycerol[b] 20° C. $\tau$ (ns) | 5° C. $\tau$ (ns) | −15° C. $\tau$ (ns) |
|---|---|---|---|---|---|
| None[c] | 375 | 521 | 472 | 459 | 466 |
| ConA | 341 | 509 | 416 | 418 | 416 |
| HSA | 336 | 467 | 392 | 467 | 485 |
| IgG | 348 | 618 | 427 | 472 | 501 |
| Ferritin | 250 | 424 | 291 | 369 | 373 |

[a]Excitation 483 nm, emission above 540 nm, (Corning 3-67 filter), air equilibrated.
[b]% glycerol by volume with buffer.
[c]Ru-free refers to Ru(bpy)$_2$(dcbpy).

The decay times increased somewhat in the presence of glycerol, and at lower temperatures, but the overall range was only about two-fold (250 to 500 ns). As might be expected, the lifetime of Ru-labeled Ferritin was somewhat smaller than that of the other proteins, which was probably due to energy transfer to the long-wavelength absorption of Ferritin. The long lifetime of these labels suggest that the Ru-complex can be used to measure rotation correlation times as long as 1.5 μs, about three times the luminescence lifetime.

One may notice that the signal/noise ratio is only modest in these data (see FIG. 8), which is due to a combination of factors including the inefficient "perylene lamp" and the slow emission rate of the complexes, which resulted in a relatively low number of counts per timing channel (from about 1000 to 3000 counts). Nonetheless, these data are adequate for these studies to determine the usefulness of these metal-ligand complexes as anisotropy probes. It is noted that while the number of photon counts per channel is low, the total number of counts is high, near 10$^6$, and the decay times are well defined from these data.

To demonstrate that the time-dependent anisotropy depends on rotational diffusion, the anisotropy of free [Ru(bpy)$_2$(dcbpy)] was examined in 60% glycerol-water (v/v) at varying temperatures and viscosities (see FIG. 9). At 20° C., the anisotropy decayed rapidly with a correlation time near 8 ns. As the temperature decreased, the anisotropy decayed more slowly, with the correlation time increasing to 240 ns at −30° C., and to over 1 μs at −51° C. (see FIG. 9). Since the lifetime of the Ru-complex is near 500 ns, the intensity only decayed to about 60% of the initial value at 240 ns. Hence, it should be possible to measure still longer correlation times. At −51° C., the correlation time was longer than 1 μs, with some evidence of a more rapid component near 115 ns. The origin of this shorter component is unknown and may reflect the role of solvent relaxation in localization of the excited state within the complex. Nonetheless, the near single exponential anisotropy decays and the apparent activation energy for rotation diffusion near 9.46 kcal/mole (using data from FIG. 9) supports the use of the Ru-complex as a rotational diffusion probe.

Time-dependent anisotropy decays of the free Ru-complex and the Ru-labeled proteins are shown in FIG. 10. For the Ru-complex alone in a buffer (i.e., not coupled to proteins), the anisotropy decayed within the 5 ns pulse width of the "perylene lamp". In contrast, the anisotropy decayed much more slowly for the Ru-labeled proteins. Importantly, the time-dependent decreases in anisotropy became slower as the molecular weight of the labeled protein increased. Specifically, Ru-labeled Ferritin displayed the slowest anisotropy decay, ConA displayed the most rapid anisotropy decay, and IgG displayed an intermediate decay. While one might expect the anisotropy decay of ConA (MW 102,000 for the tetramer) to be slower than HSA (MW 65,000), it is not known whether the ConA subunits dissociate on this timescale, and the shapes of these two proteins may differ. In any event, the data in FIG. 10 demonstrate that the anisotropy decays of the Ru-labeled proteins are sensitive to the size and/or shape of the proteins. In fact, these data have already suggested the presence of a multi-exponential anisotropy decay for IgG, in contrast to the single exponential anisotropy decays of HSA and ConA.

Additional anisotropy decays are shown in FIGS. 11A, 11B, 12A and 12B. The data for ConA and IgG demonstrate that the Ru-complex displays a slower anisotropy decay as protein rotational diffusion is slowed by adding glycerol (FIGS. 11A and 11B). At a given glycerol concentration, the anisotropy decay is slower at lower temperatures (FIGS. 12A and 12B). The longest measured correlation time was 807 ns, as estimated from the anisotropy decay of Ferritin in 30% glycerol at 5° C. Correlation times longer than 1 μs were observed, as set forth below in Table II, but they were not well resolved.

FIG. 13 shows a polarization immunoassay of human serum albumin. In this case the HSA was labeled with [Ru(bpy)$_2$dcbpy]. The labeled HSA was titrated with HSA-specific IgG. The polarization increased by approximately 200% upon binding to antibody. The open circles show the polarization measured when the labeled HSA was titrated with nonspecific antibody. In this case the fluorescence polarization remained unchanged.

FIG. 14 shows the time-dependent anisotropy decays of labeled HSA in the absence and presence of HSA-specific antibody. One notices that the anisotropy decay was much slower in the presence of HSA-specific IgG than for labeled HSA alone. This observation indicates that binding of IgG to HSA was slowing the rotational motions of the Ru-complex.

FIG. 15 shows a competitive immunoassay for HSA. In this case, HSA was labeled with the Ru-complex, and this labeled HSA was partially saturated with antibody. The presence of unlabeled HSA in the sample was observed by a decrease in the fluorescence polarization. The decrease in polarization resulted from the competitive binding of labeled and unlabeled HSA to the antibody.

FIG. 16 shows the time-dependent anisotropy decay for the competitive immunoassay. The anisotropy decayed more rapidly as the concentration of analyte (unlabeled HSA) was increased. This effect was observed because the unlabeled HSA competes for binding to the antibody, preventing the binding of labeled HSA to the antibody.

FIG. 17 shows the absorption and anisotropy spectrum of an Os complex, Os(bpy)$_2$(dcbpy). This complex displays high anisotropy in frozen solution. This indicates that this compound can also be useful as a probe for measurement of protein rotations, i.e., affinity assays. An important characteristic of the Os complex is its long wavelength absorption and emission. It can be excited with laser diodes from 600 to over 700 nm, or possibly a light emitting diode or an electroluminescent device. The extent of autofluorescence from biological samples decreases at longer excitation wavelengths.

FIG. 18 shows the emission spectrum of the Os complex. The lifetime of the Os complex is near 50 ns. This lifetime may be better than the Ru-complex (400 ns) for substances like serum albumin (MW≈70,000) with correlation times near 50 ns. The Ru-complex may be better for higher molecular weight antigens. Again, we note that there are Os complexes with decay times near 400 ns, which have the combined advantages of long wavelength excitation and emission and long decay time.

FIGS. 19 and 20 show the absorption and anisotropy spectra of a Rhenium (Re) complex. FIG. 21 shows its emission spectrum. The Re complex displays good polarization, and it should be useful in immunoassays and affinity assays.

TABLE II

Anisotropy decays of [Ru(bpy)$_2$(dcbpy)] and Ru-labeled proteins.[a]

| Protein | Buffer pH 7 20° C. θ (ns) | 60% glycerol 20° C. θ (ns) | 30% glycerol 20° C. θ (ns) | 30% glycerol 5° C. θ (ns) | 30% glycerol −15° C. θ (ns) |
|---|---|---|---|---|---|
| None | 3.9 | 8.3 | 4.4 | 5.8 | 12.1 |
| HSA | 51 | 139 | 120 | 117 | 73 |
|  | — | 15 | 14 | 13 | —[b] |
|  | — | 212 | 136 | 213 | — |
| ConA | 33 | 121 | 90 | 109 | 165 |
|  | — | 21 | 15 | 9 | 19 |
|  | — | 296 | 96 | 165 | 218 |
| IgG | 76 | 120 | 131 | 92 | 167 |
|  | 9 | 14 | 15 | 38 | 37 |
|  | 78 | 317 | 200 | 480 | >1 µs |
| Ferritin | 89 | 133 | 120 | 107 | 112 |
|  | 24 | 15 | 20 | 28 | 34 |
|  | 165 | >1 µs | 351 | 807 | >1 µs |

[a]Excitation 483 nm, emission above 540 nm, (Corning 3-67 filter), air equilibrated. The viscosities at 20° C. as estimated to be 1.02, 3.0 and 17 cP for buffer, 30% and 60% glycerol, respectively.
[b]Does not fit two components.
[c]Ru-free refers to Ru(bpy)$_2$(dcbpy).

As can be seen from the above, the polarized emission from metal-ligand complexes offers numerous experimental opportunities in biophysics and clinical chemistry. A wide range of lifetimes, absorption and emission maxima can be obtained by careful selection of the metal and the ligand. Absorption wavelengths as long as 700 nm can be obtained using osmium, and lifetimes as long as 100 ks can be obtained using rhenium as the metal in such complexes. The rhenium complexes also display good quantum yields in aqueous solution.

The anisotropy decays shown above indicate a considerable mobility of the present Ru-complex which is independent of overall rotational diffusion. If the independent motions can be decreased in amplitude, then a higher fraction of the total anisotropy will be available to detect the overall hydrodynamics of the proteins. This could be accomplished by structural variants of the [Ru(bpy)$_2$(dcbpy)]$^{2-}$ complex.

It should also be noted that such long-lived probes can be useful for studies of diffusive processes in a timescale presently not accessible by the usual fluorescence probes. For instance, there is considerable interest in the rates and amplitudes of domain-to-domain motions in proteins, and there have been repeated attempts to study such motions by time-resolved fluorescence resonance energy transfer (FRET). These measurements have been mostly unsuccessful due to the 5–10 ns decay times and the limited extent of interdomain motions on this timescale. The use of longer lived MLC emission can allow measurement of these motions.

Finally, it is noted that the MLC can provide considerable information on rotational processes using only steady-state data. The emission of these complexes can be quenched by a variety of molecules and ions, typically by photo-induced electron transfer to the quencher. The long lifetimes of these complexes suggests that the lifetimes of the labeled macromolecules can be varied over a wide range with modest concentrations of quencher. Steady-state anisotropy measurements, as a function of lifetime or quencher concentrations, can be used to determine the anisotropy decay law of membrane and protein-bound fluorophores.

While the invention has been described in detail and with reference to specific examples thereof, it will be apparent to one skilled in the art that various changes and modifications can be made therein without departing from the spirit and scope thereof.

What is claimed is:

1. A method of conducting an assay of a sample of interest, comprising the steps of:

coupling a luminescent asymmetric transition metal-ligand complex to an analyte in the sample of interest to form a coupled analyte, wherein the asymmetric transition metal-ligand complex-coupled analyte is capable of emitting polarized fluorescent light after being excited with linearly polarized electromagnetic light energy;

exciting the coupled analyte with linearly polarized electromagnetic light energy to cause the coupled analyte to emit polarized fluorescent light; and measuring the polarization of the fluorescent light emission as a measure of a biological characteristic of the analyte in the sample of interest.

2. A method of claim 1, wherein the metal in said metal-ligand complex is selected from the group consisting of ruthenium, osmium, rhenium, rhodium, iridium, tungsten and platinum.

3. A method of claim 1, wherein the analyte of interest is an antigenic substance or with a molecular weight over 2,000.

4. A method of claim 1, wherein the exciting electromagnetic energy is a linearly polarized light pulse, and the method further comprises the step of measuring the polarization of the fluorescent light only after background autoflourescence of the coupled sample has subsided.

5. A method of claim 4, wherein the exciting step is implemented by a light source selected from the group consisting of a flash lamp, a modulated lamp, an electroluminescent device, a light-emitting diode, a diode laser, and an amplitude modulated laser.

6. A method of claim 4, wherein the light pulse and the fluorescent light are transmitted through optical fibers.

7. A method of claim 1, wherein the measuring step is performed using an implanted patch containing the coupled sample.

8. A method of claim 1, wherein a steady state of polarization is dependent on a characteristic of the coupled sample or any uncoupled analyte which is present in said sample.

9. A method of claim 1, wherein intensity decay or polarization decay is dependent on the coupled analyte.

10. A method of claim 3, wherein the antigenic substance is a protein, nucleic acid, or polysaccharide.

11. A method of claim 3, wherein the antigenic substance is a cellular or cell surface antigen, glycopeptide, lipoprotein, or glycolipid.

12. A method of claim 1, wherein the amount of analyte is estimated from time-dependent anisotropy decay as measured following pulsed excitation.

13. A method of claim 1, wherein the amount of analyte is determined from emission anisotropy decay measured with amplitude-modulated excitation by phase-modulation fluorometry.

14. A method of claim 1, wherein the immunoassay is a competitive immunoassay.

15. A fluorescence polarization assay for quantifying the amount of an analyte in a sample, comprising the steps of:
   (a) mixing (1) an asymmetric transition metal-ligand complex conjugated to a molecule which specifically binds said analyte with (2) said sample, wherein the asymmetric transition metal-ligand complex is capable of emitting polarized light after being excited with linearly polarized light;
   (b) exciting the mixture of step (a) with linearly polarized light to cause the complex to emit polarized light;
   (c) measuring the polarization of the light emitted by said complex;
   (d) calculating the amount of analyte in the sample by correlating the polarization measured in step (c) with the polarization of light emitted from a control sample containing a known amount of analyte.

16. A fluorescence polarization assay of claim 15, wherein the metal in said asymmetric metal-ligand complex is selected from the group consisting of ruthenium, osmium, rhenium, rhodium, iridium, tungsten and platinum.

17. A fluorescence polarization assay of claim 15, wherein the ligand in said metal-ligand complex comprises polypyridine or bipyridine and optionally further comprises CO, Cl, phosphine, nitrile or isonitrile groups.

18. A fluorescence polarization assay of claim 17, wherein said ligand contains a reactive group selected from the group consisting of a N-hydroxysuccinimide ester of a carboxylic acid, haloacetyl groups, sulfonyl chlorides, maleimides, and isothiocyanates.

19. A fluorescence polarization assay of claim 17, wherein said molecule is a receptor, antibody or lectin.

20. A fluorescence polarization assay of claim 15, wherein the ligand in said metal-ligand complex comprises a bipyrazyl group, a phenanthroline group.

21. A competitive fluorescence polarization assay for quantifying the amount of an analyte in a sample, comprising the steps of:
   (a) mixing (1) a control containing a known amount of analyte conjugated to an asymmetric transmission metal-ligand complex with (2) a molecule which specifically binds the analyte, wherein the asymmetric transition metal-ligand complex is capable of emitting polarized light after being excited with linearly polarized light;
   (b) exciting the mixture of step (a) with linearly polarized light to cause the complex to emit polarized light;
   (c) measuring the polarization of the light emitted by the complex;
   (d) adding the sample to the mixture to form a new mixture including analyte not conjugated which competes with the analyte conjugated to the asymmetric transition metal-ligand complex in binding to the molecule which specifically binds the analyte, thereby causing a change in polarization;
   (e) measuring the change in polarization;
   (f) calculating the amount of analyte in the sample by correlating the change in polarization with the control containing a known amount of analyte.

22. A competitive fluorescence polarization immunoassay of claim 21, wherein the metal in said asymmetric metal-ligand complex is selected from the group consisting of ruthenium, osmium, rhenium, rhodium, iridium, tungsten and platinum.

23. A competitive fluorescence polarization immunoassay of claim 21, wherein the ligand in said metal-ligand complex comprises polypyridine or bipyridine.

24. A competitive fluorescence polarization immunoassay of claim 23, wherein said ligand contains a reactive group selected from the group consisting of a N-hydroxysuccinimide ester of a carboxylic acid, haloacetyl groups, sulfonyl chlorides, maleimides, and isothiocyanates.

25. A competitive fluorescence polarization immunoassay of claim 23, wherein said molecule is a receptor, antibody or lectin.

26. A competitive fluorescence polarization immunoassay of claim 21, wherein the ligand in said metal-ligand complex comprises a bipyrazyl, a phenanthroline, or a related compound and optionally further comprises CO, Cl, phosphine, nitrile or isonitrile groups.

27. A method of conducting an affinity polarization assay of a sample of interest to quantify the amount of an analyte in the sample, comprising the steps of:
   (a) mixing (1) a control containing a known amount of analyte conjugated to an asymmetric transition metal-ligand complex with (2) a molecule which has affinity for the analyte, wherein the asymmetric transition metal-ligand complex is capable of emitting polarized light after being excited with linearly polarized light;
   (b) exciting the mixture of step (a) with linearly polarized light to cause the complex to emit polarized light;
   (c) measuring the polarization of the light emitted by the complex;
   (d) adding the sample to the mixture to form a new mixture including analyte not conjugated which competes with the analyte conjugated to the asymmetric transition metal-ligand complex in associating with the molecule which has affinity for the analyte, thereby causing a change in polarization;
   (e) measuring the change in polarized emission;
   (f) calculating the amount of analyte in the sample by correlating the change in polarization with the control containing a known amount of analyte.

28. A method of claim 27, wherein the molecule which has affinity for the analyte is selected from the group consisting of strepavidin, avidin, biotin and lectins.

29. A method of claim 27, wherein the molecule which has affinity for the analyte is a protein.

30. A method of claim 27, wherein the metal in said metal-ligand complex is selected from the group consisting of ruthenium, osmium, rhenium, rhodium, iridium, tungsten and platinum.

* * * * *